United States Patent
Itoh et al.

(10) Patent No.: US 6,673,570 B1
(45) Date of Patent: Jan. 6, 2004

(54) SMAD ASSOCIATING POLYPEPTIDES

(75) Inventors: Fumiko Itoh, Uppsala (SE); Susumu Itoh, Uppsala (SE); Carl-Henrik Heldin, Uppsala (SE); Peter ten Dijke, Amsterdam (NL)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/665,479

(22) Filed: Sep. 20, 2000

Related U.S. Application Data

(60) Provisional application No. 60/154,846, filed on Sep. 20, 1999.

(51) Int. Cl.[7] .................. C12P 21/06; C07H 17/00; C07K 14/00
(52) U.S. Cl. ............. 435/69.1; 435/320.1; 435/252.3; 435/325; 536/23.1; 530/350
(58) Field of Search .................. 435/320.1, 325, 435/252.3, 69.1; 536/23.1; 530/350

(56) References Cited

FOREIGN PATENT DOCUMENTS

| WO | WO 98/54963 | * | 6/1998 | .......... A01N/37/18 |
|---|---|---|---|---|
| WO | WO 98/53068 A1 | | 11/1998 | |
| WO | WO 98/55512 A2 | | 12/1998 | |
| WO | WO 98/56913 A1 | | 12/1998 | |
| WO | WO 01/10903 | * | 8/2000 | .......... C12N/15/57 |

OTHER PUBLICATIONS

Hata et al., Genes & Devel. 12: 186–197 (1998).
Zhu et al., Nature 400: 687–693 (1999).
Bartel et al., Cellular Interactions in Devel., 153–179 (1994).
Funakoshi et al., EMBO J. 18(18): 50009–5018 (1999).
Mah et al., GenBank acc. No. AF176069, GI:5733823 (2000).
Mah et al., J of Cell Biology 151(14): 847–862 (2000).
Mah et al., *Mol. Biol. of the Cell* 9(Supp): 183a– abstr. 1056 (1998).
Mah et al., *Mol. Biol. of the Cell* 10(Supp): 270a– abstr. 1563 (1999).
GenBank accession No. A1379212, Jan. 28, 1999.
Bai et al., J. of Bone and Min. Res. 14(Suppl 1): S146– Abst. 1053 (1999).
Kleijnen et al., *Mol. Cell.* 6: 409–419 (2000).

* cited by examiner

Primary Examiner—Karen Cochrane Carlson
(74) Attorney, Agent, or Firm—Wolf, Greenfield & Sacks, P.C.

(57) ABSTRACT

The invention describes Smad associating proteins (SAPs) and nucleic acids that encode SAPs, including fragments and biologically functional variants thereof, as well as antibodies that bind thereto. Methods and products for using such nucleic acids and polypeptides also are provided.

20 Claims, 4 Drawing Sheets

| Clone No. | Clone Name | Number | ShortSmad6 | ShortSmad6N | ShortSmad6C | Smad7 | Smad7N | Smad7C | Smad2 | Smad4 |
|---|---|---|---|---|---|---|---|---|---|---|
| 2 | AMSH(SAP1) | 39 | +++ | +++ | - | +++ | ++ | +++ | - | - |
| 8 | STAM | 2 | +++ | +++ | - | +++ | + | ++ | - | - |
| 14 | Hsp40 homolog | 1 | - | +++ | +++ | - | - | - | + | - |
| 15 | SAP4 | 1 | +++ | +++ | - | +++ | - | +++ | - | - |
| 25 | Dodecenoyl-CoA | 1 | - | - | - | - | - | - | - | - |
| 26 | SAP5 | 1 | +++ | +++ | - | +++ | - | - | - | - |
| 30 | Uba80 | 5 | +++ | - | - | +++ | - | +++ | - | - |
| 31 | Tax-1 binding protein | 3 | + | - | - | +++ | + | + | - | + |
| 32 | SAP2 | 10 | +++ | +++ | ++ | +++ | - | +++ | - | - |
| 37 | AMSH(SAP1) (different from clone 2) | 2 | ++ | +++ | - | +++ | +++ | + | - | - |
| 57 | Rabaptin-5 | 2 | +++ | +++ | + | +++ | - | - | - | - |
| 59 | 26S proteinase S5a | 1 | +++ | +++ | - | +++ | +++ | ++ | ++ | - |
| 60 | SAP3 | 2 | +++ | +++ | - | +++ | - | +++ | ++ | - |
| 61 | Tax-1 binding protein (different from clone 31) | 2 | +++ | +++ | + | +++ | + | ++ | +++ | - |
| 72 | SAP2 (different from clone 32 and 93) | 1 | +++ | +++ | - | +++ | - | ++ | - | - |
| 93 | SAP2 (different from clones 32 and 72) | 1 | +++ | +++ | - | +++ | - | ++ | - | - |
| 98 | Rabaptin-5 (different from clone 57) | 1 | +++ | +++ | ++ | +++ | +++ | ++ | + | - |

FIG. 2

SMAD ASSOCIATING POLYPEPTIDES

RELATED APPLICATIONS

This application claims priority under 35 U.S.C. §119 from U.S. provisional application serial No. 60/154,846, filed Sep. 20, 1999.

FIELD OF THE INVENTION

This invention relates to nucleic acids and encoded polypeptides which interact with Smad proteins. The invention also relates to agents which bind the nucleic acids or polypeptides. The invention further relates to methods of using such nucleic acids and polypeptides in the treatment and/or diagnosis of disease.

BACKGROUND OF THE INVENTION

Members of the transforming growth factor-β (TGF-β) family are multifunctional cytokines with elicit a wide range of cellular effects, including growth inhibition, differentiation and apoptosis (Heldin et al., *Nature* 390:465–471, 1997). The signaling induced by TGF-β family members are initiated through a heteromeric transmembrane kinase complex that consists of type I and type II receptors. The activated type I receptor induces the phosphorylation of receptor-activated Smads (R-Smads) which heteromerize with Smad4. These complexes translocate from the cytoplasm to the nucleus to direct transcriptional regulation of responsive genes (Heldin et al., 1997).

Recently, Smad6 and Smad7 were isolated, which form a subfamily among the Smads and function to inhibit the intracellular signaling by R-Smad/Smad4 complexes. Smad6 and Smad7 constitutively associate with type I receptor by blocking association and phosphorylation of R-Smads (Hayashi et al., *Cell* 89:1165–1173, 1997; Imamura et al., *Nature* 389:622–626, 1997; Nakao et al., *Nature* 389:631–635, 1997). Smad6 and Smad7 are rapidly induced by members of the TGF-β family (Afrakhte et al., *Biochem. Biophys. Res. Commun.* 249:505–511, 1998), suggesting that inhibitory Smads may take part in a negative feedback control mechanism to modulate the signaling induced by members of TGF-β family.

The central role of Smads and TGF-β in cellular processes presents a need for additional factors to modulate Smads and TGF-β interactions with signal transduction pathways.

SUMMARY OF THE INVENTION

Using the yeast two hybrid system, proteins that specifically bind with Smad6 and Smad7 have been isolated. The invention provides these isolated Smad associating proteins (SAPs) and fragments of those molecules, as well as agents which bind such polypeptides, including antibodies. The invention also provides nucleic acid molecules encoding SAPs, unique fragments of those molecules, expression vectors containing the foregoing, and host cells transfected with those molecules. The foregoing can be used in the diagnosis or treatment of conditions characterized by the expression of a Smad associating protein, or in the treatment of conditions characterized by the expression of a SAP, or in the treatment of a condition characterized by the expression of a Smad nucleic acid or polypeptide, or by the inadequate or excessive activity of a Smad polypeptide. The invention also provides methods for identifying pharmacological agents useful in the diagnosis or treatment of such conditions. Here, the identification of several SAPs is presented. The SAPs bind to Smad polypeptides including Smad6 and Smad7 and thus are components of TGF-β superfamily signaling pathways.

According to one aspect of the invention, isolated nucleic acid molecules are provided. The isolated nucleic acid molecules are nucleic acid molecules which hybridize under stringent conditions to a molecule consisting of the nucleic acid sequence set forth in SEQ ID NO:3 or SEQ ID NO:5 and which code for a polypeptide which binds Smad6, or nucleic acid molecules that differ from the foregoing nucleic acid molecules in codon sequence due to the degeneracy of the genetic code, or complements of the foregoing nucleic acid molecules. Preferably the isolated nucleic acid molecule consists of SEQ ID NO:3 or SEQ ID NO:5.

According to another aspect of the invention, isolated nucleic acid molecules are provided which are unique fragments of nucleotides 1–2399 of SEQ ID NO:3 between 12 and 2398 nucleotides in length or of nucleotides 1–855 of SEQ ID NO:5 between 12 and 854 nucleotides in length. Also provided are complements of the foregoing unique fragments provided that the nucleic acid molecule excludes sequences consisting of GenBank accession numbers AF176069, AF293384, AA305358, AI219112, N33797 and AB030502. In certain embodiments, the isolated nucleic acid molecule consists of at least 22, 25, 30, 40, 50, 75 or 100 contiguous nucleotides. In other embodiments, the isolated nucleic acid molecule consists of between 20 and 32 contiguous nucleotides.

According to still another aspect of the invention, expression vectors including any of the foregoing isolated nucleic acid molecules operably linked to a promoter are provided. Also provided are host cells transformed or transfected with the expression vectors, as well as transgenic non-human animals including the expression vectors.

According to yet another aspect of the invention, methods for producing a polypeptide are provided. The methods include culturing the foregoing host cells under conditions which permit the expression of polypeptide. Preferably the methods include isolating the polypeptide.

In another aspect of the invention, isolated polypeptides are provided which are encoded by the foregoing isolated nucleic acid molecules. Preferred isolated polypeptides include molecules comprising the amino acid sequences of SEQ ID NO:4, SEQ ID NO:6, fragments or functional variants of SEQ ID NO:4, and a fragments or functional variants of SEQ ID NO:6.

According to still another aspect of the invention, isolated polypeptides are provided which include a fragment or functional variant of SEQ ID NO:2. In certain embodiments the fragment of SEQ ID NO:2 consists of amino acids 1–101+234–424, 106–424 or 234–424.

According to yet another aspect of the invention, an isolated complex of polypeptides is provided. The complex includes one of the foregoing polypeptide bound to a polypeptide selected from the group consisting of Smad6, Smad7 and fragments thereof.

Also included as an aspect of the invention are isolated polypeptides which bind selectively a polypeptide encoded by the foregoing isolated nucleic acid molecules, provided that the isolated polypeptide is not a Smad, STAM or cyclin polypeptide. In certain embodiments, the isolated polypeptide binds to an epitope defined by a polypeptide consisting of the sequence of SEQ ID NOs:2, 4 or 6. In other embodiments, the isolated polypeptide is an antibody fragment selected from the group consisting of a Fab fragment, a F(ab)$_2$ fragment or a fragment including a CDR3 region selective for a SAP polypeptide. In still other embodiments the isolated polypeptide is a monoclonal antibody, a humanized antibody or a chimeric antibody.

According to still another aspect of the invention, methods for modulating TGF-β superfamily signal transduction in a mammalian cell are provided. The methods include contacting the mammalian cell with an amount of an agent which increases the amount of a Smad associating protein selected from the group consisting of SAP1/AMSH (SEQ ID NO:2), SAP2 (SEQ ID NO:4), SAP3 (SEQ ID NO:6), Hsp40 homolog (U40992; SEQ ID NO:8), Uba80 (X63237; SEQ ID NO:10), Tax-1 binding protein (U33822; SEQ ID NO:12), rabaptin-5 (NM_004703; SEQ ID NO:14), and 26S proteinase S5a (U51007; SEQ ID NO:16) or a fragment thereof in the cell effective to reduce TGF-β superfamily signal transduction in the mammalian cell. In certain embodiments, the agent is a nucleic acid molecule encoding one of the foregoing polypeptides.

According to another aspect of the invention, methods for regulating the cell cycle in a mammalian cell are provided. The methods include contacting the mammalian cell with an amount of an agent which increases the amount of SAP2 (SEQ ID NO:4), or a fragment thereof, in the cell effective to bind a cyclin and regulate the cell cycle in the mammalian cell.

In further aspects of the invention, methods for identifying lead compounds for a pharmacological agent are provided. In certain embodiments, the methods include forming a mixture comprising a Smad6 or Smad7 polypeptide, a SAP polypeptide, and a candidate pharmacological agent, incubating the mixture under conditions which, in the absence of the candidate pharmacological agent, permit a first amount of specific binding of the SAP polypeptide by the Smad6 or Smad7 polypeptide, and detecting a test amount of the specific binding of the SAP polypeptide by the Smad6 or Smad7 polypeptide. A reduction of the test amount of specific binding relative to the first amount of specific binding indicates that the candidate pharmacological agent is a lead compound for a pharmacological agent which disrupts the Smad6-SAP or Smad7-SAP binding, and an increase of the test amount of specific binding relative to the first amount of specific binding indicates that the candidate pharmacological agent is a lead compound for a pharmacological agent which enhances the Smad6-SAP or Smad7-SAP binding. Preferably the SAP polypeptide is selected from the group consisting of SAP1/AMSH, SAP2, SAP3 and fragments thereof.

In other embodiments, the methods include forming a mixture comprising an ALK kinase, a Smad polypeptide, a SAP polypeptide, and a candidate pharmacological agent, incubating the mixture under conditions which, in the absence of the candidate pharmacological agent, permit a first amount of specific binding of the SAP polypeptide by the Smad polypeptide, and detecting a test amount of the specific binding of the SAP polypeptide by the Smad polypeptide. A reduction of the test amount of specific binding relative to the first amount of specific binding indicates that the candidate pharmacological agent is a lead compound for a pharmacological agent which disrupts the Smad-SAP binding, and an increase of the test amount of specific binding relative to the first amount of specific binding indicates that the candidate pharmacological agent is a lead compound for a pharmacological agent which enhances the Smad-SAP binding. In preferred embodiments, the SAP polypeptide is selected from the group consisting of SAP1/AMSH, SAP2, SAP3 and fragments thereof, the Smad polypeptide is selected from the group consisting of Smad2, Smad3, Smad4, Smad6, Smad7 and fragments thereof, and the ALK kinase is selected from the group consisting of ALK5, constitutively activated ALK5, ALK6, constitutively activated ALK6 and fragments thereof having kinase activity.

The use of the foregoing compositions in the preparation of a medicament is also contemplated.

These and other aspects of the invention will be described in further detail in connection with the detailed description of the invention.

BRIEF DESCRIPTION OF THE FIGURES

FIG. 2 shows the evaluation of Smad6-associating proteins using yeast two hybrid assay. Smad2, Smad4, Smad6S and Smad7 were used as baits to examine interaction with Smad6-associating proteins in yeast.

BRIEF DESCRIPTION OF THE SEQUENCES

Figure 1:
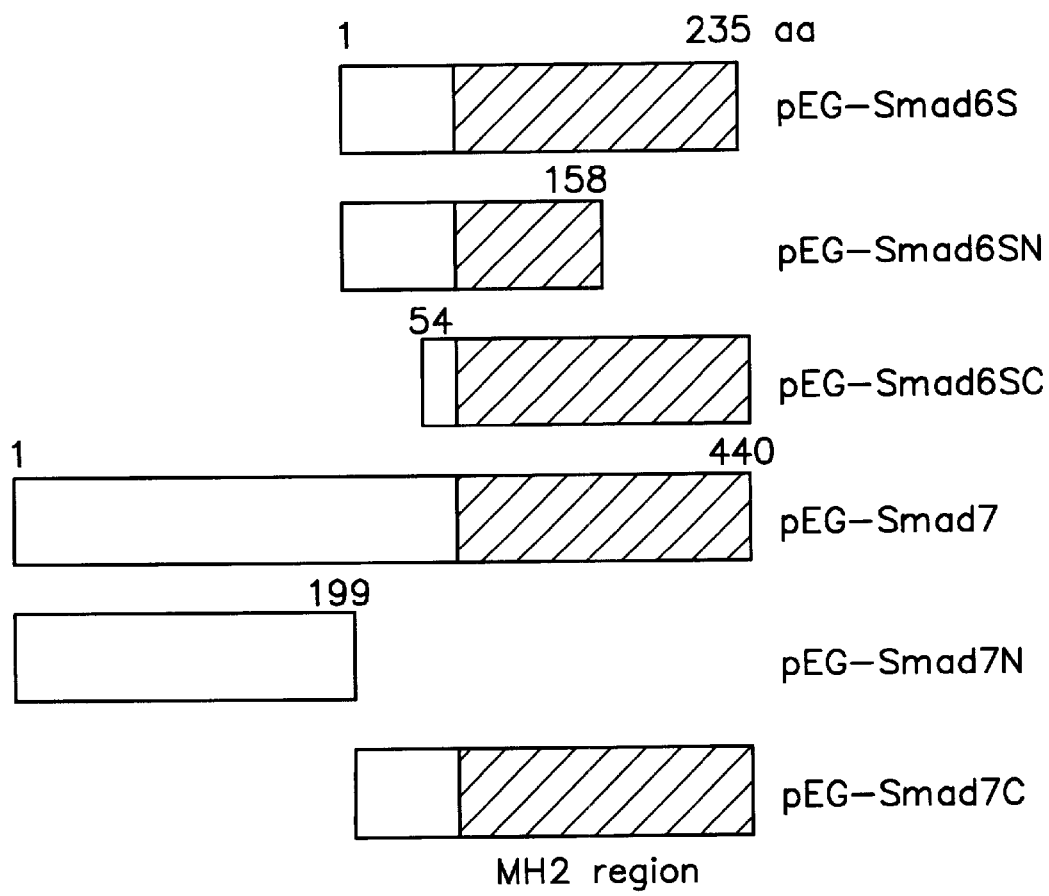
FIG. 1 depicts a schematic structures of Smad6S and Smad7 mutants used in the yeast two hybrid assay. The human short form of Smad6 and mouse Smad7 were inserted into pEG202.

SEQ ID NO:1 is the nucleotide sequence of human SAP1/AMSH.

SEQ ID NO:2 is the amino acid sequence of human SAP1/AMSH.

SEQ ID NO:3 is the nucleotide sequence of human SAP2.

SEQ ID NO:4 is the amino acid sequence of human SAP2.

SEQ ID NO:5 is the nucleotide sequence of human SAP3.

SEQ ID NO:6 is the amino acid sequence of human SAP3.

SEQ ID NO:7 is the nucleotide sequence of the Hsp40 homolog having GenBank accession number U40992.

SEQ ID NO:8 is the amino acid sequence of the Hsp40 homolog having GenBank accession number U40992.

SEQ ID NO:9 is the nucleotide sequence of Uba80, having GenBank accession number X63237.

SEQ ID NO:10 is the amino acid sequence of Uba80, having GenBank accession number X63237.

SEQ ID NO:11 is the nucleotide sequence of Tax-1 binding protein, having GenBank accession number U33822.

SEQ ID NO:12 is the amino acid sequence of Tax-1 binding protein, having GenBank accession number U33822.

SEQ ID NO:13 is the nucleotide sequence of rabaptin-5, having GenBank accession number NM_004703.

SEQ ID NO:14 is the amino acid sequence of rabaptin-5, having GenBank accession number NM_004703.

SEQ ID NO:15 is the nucleotide sequence of the 26S proteinase S5a, having GenBank accession number U51007.

SEQ ID NO:16 is the amino acid sequence of the 26S proteinase S5a, having GenBank accession number U51007.

DETAILED DESCRIPTION OF THE INVENTION

The present invention in one aspect involves the cloning of cDNAs encoding several Smad associating proteins (SAPs). The sequence of the human nucleic acids for SAP1, SAP2 and SAP3 are presented as SEQ ID NOs:1, 3 and 5, respectively, and the predicted amino acid sequences of the protein products are presented as SEQ ID NOs:2, 4 and 6. Analysis of the sequences by comparison to nucleic acid and protein databases determined that SAP1 corresponds to the human AMSH gene (GenBank accession numbers NM_006463, U73522) and that SAP2 is related to a Xenopus gene, XDRP1 (Funakoshi et al., *EMBO J.* 18:5009–5018, 1999). To the extent that the SAP polypeptides identified herein are similar to previously identified sequences, it is entirely unexpected that the polypeptides are binding partners for Smad proteins.

The invention thus involves in one aspect SAP polypeptides, genes encoding those polypeptides, functional modifications and variants of the foregoing, useful fragments of the foregoing, as well as therapeutics relating thereto. The expression of these genes affects TGF-β superfamily signal transduction by binding to Smad polypeptides including Smad6 and Smad7. The TGF-β superfamily members are well known to those of ordinary skill in the art and include TGF-βs, activins, bone morphogenetic proteins (BMPs), Vg1, Mullerian inhibitory substance (MIS) and growth/differentiation factors (GDFs).

Homologs and alleles of the Smad associating protein-encoding nucleic acids of the invention can be identified by conventional techniques. Thus, an aspect of the invention is those nucleic acid sequences which code for SAP polypeptides and which hybridize to a nucleic acid molecule consisting of the coding region of SEQ ID NO:1, SEQ ID NO:3 or SEQ ID NO:5, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1–0.5×SSC/0.1× SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of SAP nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity and/or at least 90% amino acid identity to SEQ ID NOs:1, 3 or 5 and SEQ ID NOs:2, 4 or 6, respectively, in some instances will share at least 90% nucleotide identity and/or at least 95% amino acid identity and in still other instances will share at least 95% nucleotide identity and/or at least 99% amino acid identity. The homology can be calculated using various, publicly available software tools developed by National Center for Biotechnology Information (NCBI) (Bethesda, Md.) that can be obtained through the Internet. Exemplary tools include the BLAST system available from the NCBI, preferably using default settings. Pairwise and ClustalW alignments (BLOSUM30 matrix setting) as well as Kyle-Doolittle hydropathic analysis can be obtained using the Mac vector sequence analysis software (Oxford Molecular Group). Watson-Crick complements of the foregoing nucleic acids also are embraced by the invention.

In screening for nucleic acids encoding Smad associating proteins with sequence homology to the SAP nucleic acids described herein, a Southern blot may be performed using the foregoing conditions, together with a radioactive probe. After washing the membrane to which the DNA is finally transferred, the membrane can be placed against X-ray film to detect the radioactive signal.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Smad7 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as Smad binding, antigenicity, enzymatic activity, receptor binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides isolated unique fragments of SEQ ID NOs:1, 3 or 5 or complements of SEQ ID NOs:1, 3 or 5 of sufficient length to represent a sequence unique within the human genome, and identifying a nucleic acid encoding a Smad associating polypeptide. A unique fragment is one that is a 'signature' for the larger nucleic acid. It, for example, is long enough to assure that its precise sequence is not found in molecules outside of the SAP nucleic acids defined above. A unique fragment includes a sequence of contiguous nucleotides which is not identical to any sequence selected from the sequence group consisting of (1) sequences having the GenBank accession numbers AF176069, AF293384, AA305358, A1219112, N33797, AB030502 and other sequences publicly available as of the filing date of this application, (2) complements of (1), and (3) fragments of (1) and (2). Thus a unique fragment excludes, by definition, sequences consisting solely of EST and/or gene sequences such as those described by GenBank accession numbers AF176069, AF293384, AA305358, A1219112, N33797 and AB030502.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern blot assays to identify such nucleic acids, or can be used in amplification assays such as those employing PCR. As known to those skilled in the art, large probes such as 200, 250, 300 or more nucleotides are preferred for certain uses such as Southern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the SAP polypeptides such as the N-terminal and C-terminal fragments disclosed herein, useful, for example, in the preparation of antibodies, in immunoassays, and as a competitive binding partner of the SAPs and/or other polypeptides which bind to Smad6 or Smad7 polypeptides, for example, in therapeutic applications. Unique fragments further can be used as antisense molecules to inhibit the expression of SAP nucleic acids and polypeptides, particularly for therapeutic purposes as described in greater detail below.

As will be recognized by those skilled in the art, the size of the unique fragment will depend upon its conservancy in the genetic code. Thus, some regions of SEQ ID NOs:1, 3 and/or SEQ ID NO:5 and its complement will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 bases long). This disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide (provided the sequence is unique as described above). Many segments of SEQ ID NO:3 or SEQ ID NO:5, or complements thereof, that are 25 or more nucleotides in length will be unique. Those skilled in the art are well versed in methods for selecting such sequences, typically on the basis of the ability of the unique fragment to selectively distinguish the sequence of interest from non-SAP nucleic acids. A comparison of the sequence of the fragment to those on known data bases typically is all that is necessary, although in vitro confirmatory hybridization and sequencing analysis may be performed.

A unique fragment can be a functional fragment. A functional fragment of a nucleic acid molecule of the invention is a fragment which retains some functional property of the larger nucleic acid molecule, such as coding for a functional polypeptide, binding to proteins (e.g., Smads), regulating transcription of operably linked nucleic acids, and the like. One of ordinary skill in the art can readily determine using the assays described herein and those well known in the art to determine whether a fragment is a functional fragment of a nucleic acid molecule using no more than routine experimentation.

As mentioned above, the invention embraces antisense oligonucleotides that selectively bind to a nucleic acid molecule encoding a SAP polypeptide, to modulate TGF-β, activin and/or BMP signaling by reducing the amount of SAPs. This is desirable in virtually any medical condition wherein a reduction of SAP binding to Smad proteins is desirable, e.g., to modulate Smad activity such as in TGF-β signaling.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NOs:1, 3 or 5, or upon allelic or homologous genomic and/or cDNA sequences, or upon the nucleotide sequences of other Smad associating polypeptides disclosed herein, one of skill in the art can easily choose and synthesize any of a number of appropriate antisense molecules for use in accordance with the present invention. For example, a "gene walk" comprising a series of oligonucleotides of 15–30 nucleotides spanning the length of a SAP nucleic acid can be prepared, followed by testing for inhibition of SAP expression. Optionally, gaps of 5–10 nucleotides can be left between the oligonucleotides to reduce the number of oligonucleotides synthesized and tested.

In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although SEQ ID Nos:1, 3 or 5 disclose cDNA sequences, one of ordinary skill in the art may easily derive the genomic DNA corresponding to the cDNA of SEQ ID Nos:1, 3 or 5. Thus, the present invention also provides for antisense oligonucleotides which are complementary to the genomic DNA corresponding to SEQ ID Nos:1, 3 or 5. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding SAP polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a SAP polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for 20 example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Wamier et al., in intradermal injection in mice for immunization against P1A (*Int. J. Cancer*, 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also permits the construction of SAP gene "knock-outs" in cells and in animals, providing materials for studying certain aspects of TGF-β, activin and/or BMP signal transduction.

Figure 5:
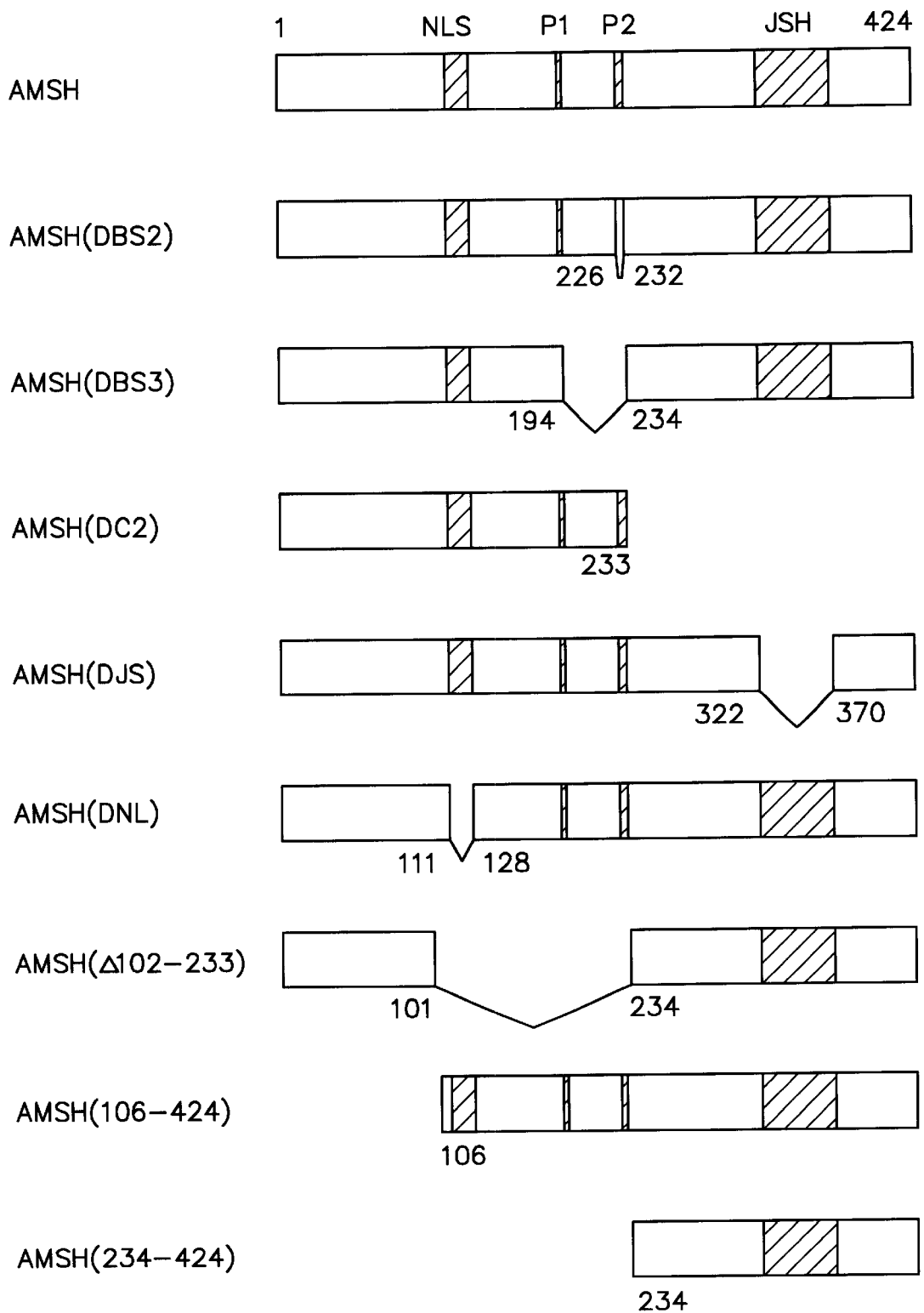
FIG. 5 shows a schematic illustration of SAP 1/AMSH mutants. NLS, putative nuclear localization signal; P1 and P2, proposed SH3 binding regions; JSH, JAB1 subdomain homologous regions.

The invention also provides isolated polypeptides, which include the polypeptides of SEQ ID NOs:2, 4 and 6 and unique fragments of SEQ ID NOs:2, 4 and 6 including fragments shown in FIG. 5 (amino acids 1–226/232–424, 1–194/234–424, 1–233, 1–322/370–424, 1–111/128–424, 1–101/234–424, 106–424 and 234–424 of SEQ ID NO:2). Such polypeptides are useful, for example, alone or as fusion proteins to test Smad binding, to test phosphorylation, to generate antibodies, and as a components of an immunoassay.

A unique fragment of a SAP polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NOs:2, 4 and/or 6 will require longer segments to be unique while others will require only short segments, typically between 5 and 12 amino acids (e.g. 5, 6, 7, 8, 9, 10, 11 and 12 amino acids long). Virtually any segment of SEQ ID NOs:4 and 6 that is 10 or more amino acids in length will be unique.

Unique fragments of a polypeptide preferably are those fragments which retain a distinct functional capability of the polypeptide. Functional capabilities which can be retained in a unique fragment of a polypeptide include binding of Smad6 and/or Smad7, interaction with antibodies, interaction with other polypeptides (such as TβR-I) or fragments thereof, selective binding of nucleic acids or proteins, and enzymatic activity. For example, as exemplified herein, N-terminal and C-terminal SAP1/AMSH fragments such as those depicted in FIG. 5 can be used as a functional equivalent of full length SAP1/AMSH in the methods of the invention, including e.g., binding of Smads for modulation of TGF-β signal transduction. Other SAP polypeptide fragments, e.g., other N-terminal or C-terminal fragments, can be selected according to their functional properties. For example, one of ordinary skill in the art can prepare SAP fragments recombinantly and test those fragments according to the methods exemplified below, such as binding to a Smad polypeptide. Those skilled in the art also are well versed in methods for selecting unique amino acid sequences, typically on the basis of the ability of the unique fragment to selectively distinguish the sequence of interest from non-family members. A comparison of the sequence of the fragment to those on known data bases typically is all that is necessary.

The invention embraces variants of the SAP polypeptides described above. As used herein, a "variant" of a SAP polypeptide is a polypeptide which contains one or more modifications to the primary amino acid sequence of a SAP polypeptide. Modifications which create a SAP variant can be made to a SAP polypeptide 1) to reduce or eliminate an activity of a SAP polypeptide, such as binding to a Smad polypeptide; 2) to enhance a property of a SAP polypeptide, such as protein stability in an expression system or the stability of protein-protein binding; or 3) to provide a novel activity or property to a SAP polypeptide, such as addition of an antigenic epitope or addition of a detectable moiety. Modifications to a SAP polypeptide are typically made to the nucleic acid which encodes the SAP polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the SAP amino acid sequence.

In general, variants include SAP polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a SAP polypeptide by eliminating proteolysis by proteases in an expression system (e.g., dibasic amino acid residues in yeast expression systems in which KEX2 protease activity is present).

Mutations of a nucleic acid which encode a Smad7 polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant SAP polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a SAP gene or cDNA clone to enhance expression of the polypeptide. The activity of variants of SAP polypeptides can be tested by cloning the gene encoding the variant SAP polypeptide into a bacterial or mammalian expression vector, introducing the vector into an appropriate host cell, expressing the variant SAP polypeptide, and testing for a functional capability of the SAP polypeptides as disclosed herein. For example, the variant Smad7 polypeptide can be tested for Smad binding as disclosed in the Examples. Preparation of other variant polypeptides may favor testing of other activities, as will be known to one of ordinary skill in the art.

The skilled artisan will also realize that conservative amino acid substitutions may be made in SAP polypeptides to provide functionally equivalent variants of the foregoing polypeptides, i.e, the variants retain the functional capabilities of the SAP polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the SAP polypeptides include conservative amino acid substitutions of SEQ ID NOs:2, 4 or 6. Conservative substitutions of amino acids include substitutions made amongst amino acids within the following groups: (a) M, I, L, V; (b) F, Y, W; (c) K, R, H; (d) A, G; (e) S, T; (f) Q, N; and(g) E, D.

Conservative amino-acid substitutions in the amino acid sequence of SAP polypeptides to produce functionally equivalent variants of SAP polypeptides typically are made by alteration of a nucleic acid encoding a SAP polypeptide (SEQ ID NOs:1, 3 and 5). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. USA*. 82: 488–492, 1985), or by chemical synthesis of a gene encoding a SAP polypeptide. Where amino acid substitutions are made to a small unique fragment of a SAP polypeptide, such as a Smad or SH3 binding site peptide, the substitutions can be made by directly synthesizing the peptide. The activity of functionally equivalent fragments of SAP polypeptides can be tested by cloning the gene encoding the altered SAP polypeptide into a bacterial or mammalian expression vector, introducing the vector into an appropriate host cell, expressing the altered SAP polypeptide, and testing for a functional capability of the SAP polypeptides as disclosed herein. Peptides which are chemically synthesized can be tested directly for function, e.g., for binding to Smad6 and/or Smad7.

The invention as described herein has a number of uses, some of which are described elsewhere herein. First, the invention permits isolation of the SAP protein molecules (SEQ ID NOs:2, 4 and 6). A variety of methodologies well-known to the skilled practitioner can be utilized to obtain isolated SAP molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating SAP polypeptides. These include, but are not limited to, immunochromatography, HPLC, size-exclusion chromatography, ion-exchange chromatography and immune-affinity chromatography.

The isolation of the SAP gene also makes it possible for the artisan to diagnose a disorder characterized by expression of SAP. These methods involve determining expression of the SAP gene, and/or SAP polypeptides derived therefrom. In the former situation, such determinations can be carried out via any standard nucleic acid determination assay, including the polymerase chain reaction as exemplified in the examples below, or assaying with labeled hybridization probes.

The invention also makes it possible isolate proteins such as Smad6 and Smad7 by the binding of such proteins to SAP as disclosed herein. The identification of this binding by SAP1, for example, also permits one of skill in the art to block the binding of Smad7 or Smad7 to other Smad-binding proteins, such as other SAPs, such as SAP2 or SAP3. Other SAPs can likewise by used to modulate protein binding to Smads. Binding of the proteins can be effected by introducing into a biological system in which the proteins bind (e.g., a cell) a SAP polypeptide including a Smad6 or Smad7 binding site in an amount sufficient to block the binding. The identification of Smad binding sites in SAPs also enables one of skill in the art to prepare modified proteins, using standard recombinant DNA techniques, which can bind to proteins such as Smad6 and Smad7. For example, when one desires to target a certain protein to a Smad6 or Smad7 protein complex, one can prepare a fusion polypeptide of the protein and a SAP protein or a fragment thereof having a Smad binding site. Additional uses are described herein.

The invention further provides methods for reducing or increasing TGF-β family signal transduction in a cell. Such methods are useful in vitro for altering the TGF-β signal transduction, for example, in testing compounds for potential to block aberrant TGF-β signal transduction or increase deficient TGF-β signal transduction. In vivo, such methods are useful for modulating growth, e.g., to treat cancer and fibrosis. Such methods also are useful in the treatment of conditions which result from excessive or deficient TGF-β signal transduction. TGF-β signal transduction can be measured by a variety of ways known to one of ordinary skill in the art, such as the reporter systems described in the references cited in the Examples. Various modulators of SAP protein activity can be screened for effects on TGF-β signal transduction using the methods disclosed herein. The skilled artisan can first determine the modulation of a SAP activity, such as Smad binding or TGF-β signaling activity, and then apply such a modulator to a target cell or subject and assess the effect on the target cell or subject. For example, in screening for modulators of SAPs useful in the treatment of cancer, cells in culture can be contacted with SAP modulators and the increase or decrease of growth or focus formation of the cells can be determined according to standard procedures. SAP activity modulators can be assessed for their effects on other TGF-β signal transduction downstream effects by similar methods in many cell types. The foregoing also applies to signaling via activin and BMP complexes.

The invention also provides, in certain embodiments, "dominant negative" polypeptides derived from SEQ ID NOs:2, 4 and/or 6. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of a SAP polypeptides, one of ordinary skill in the art can modify the sequence of the SAP polypeptides by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected activity (e.g., Smad6 binding, modulation of TGF-β signaling activity) and/or for retention of such an activity. Other similar methods for creating and testing dominant negative variants of a protein will be apparent to one of ordinary skill in the art.

Dominant negative SAP proteins can include variants in which a portion of the Smad binding site has been mutated or deleted to reduce or eliminate SAP interaction with Smad6 or Smad7. Other examples include SAP variants in which the ability to accept phosphorylation by MAP kinases is reduced. One of ordinary skill in the art can readily prepare and test SAP variants bearing mutations or deletions in various portions of the polypeptide.

The invention also involves agents such as polypeptides which bind to SAP polypeptides and to complexes of SAP polypeptides and binding partners such as Smad6 and Smad7. Such binding agents can be used, for example, in screening assays to detect the presence or absence of SAP polypeptides and complexes of SAP polypeptides and their binding partners and in purification protocols to isolate SAP polypeptides and complexes of SAP polypeptides and their binding partners. Such agents also can be used to inhibit the native activity of the SAP polypeptides or their binding partners, for example, by binding to such polypeptides, or their binding partners or both.

The invention, therefore, embraces peptide binding agents which, for example, can be antibodies or fragments of antibodies having the ability to selectively bind to SAP polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to SAP polypeptides, and complexes of both SAP polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the SAP polypeptide. This process can be repeated through several cycles of reselection of phage that bind to the SAP polypeptide. Repeated rounds lead to enrichment of phage bearing particular sequences. DNA sequence analysis can be conducted to identify the sequences of the expressed polypeptides. The minimal linear portion of the sequence that binds to the SAP polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the SAP polypeptides. Thus, the SAP polypeptides of the invention, or a fragment thereof, can be used to screen peptide libraries, including phage display libraries, to identify and select peptide binding partners of the SAP polypeptides of the invention. Such molecules can be used, as described, for screening assays, for purification protocols, for interfering directly with the functioning of SAP and for other purposes that will be apparent to those of ordinary skill in the art.

A SAP polypeptide, or a fragment thereof, also can be used to isolate their native binding partners, including, e.g., Smad6, Smad7 and complexes containing those proteins. Isolation of such binding partners may be performed according to well-known methods. For example, isolated SAP polypeptides can be attached to a substrate (e.g., chromatographic media, such as polystyrene beads, or a filter), and then a solution suspected of containing a Smad6, Smad7 or complex thereof may be applied to the substrate. If a SAP binding partner which can interact with SAP polypeptides is present in the solution, then it will bind to the substrate-bound SAP polypeptide. The SAP binding partner then may be isolated. Other proteins which are binding partners for SAP, such as other Smads, cyclin A, etc., may be isolated by similar methods without undue experimentation.

It will also be recognized that the invention embraces the use of SAP cDNAs sequences in expression vectors, as well as to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples include keratinocytes, peripheral blood leukocytes, bone marrow stem cells and embryonic stem cells. The expression vectors require that the pertinent sequence, i.e., those nucleic acids described supra, be operably linked to a promoter.

The invention also includes transgenic non-human animals. As used herein, "transgenic non-human animals" includes non-human animals having one or more exogenous nucleic acid molecules incorporated in germ line cells and/or somatic cells. Thus the transgenic animal include "knock-out" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination can be facilitated by the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to SAP nucleic acid molecules to increase expression of SAP in a regulated or conditional manner. Trans-acting negative regulators of SAP activity or expression also can be operably linked to a conditional promoter as described above. Such trans-acting regulators include antisense SAP nucleic acids molecules, nucleic acid molecules which encode dominant negative SAP molecules, ribozyme molecules specific for SAP nucleic acids, and the like. The transgenic non-human animals are useful in experiments directed toward testing biochemical or physiological effects of diagnostics or therapeutics for conditions characterized by increased or decreased SAP expression. Other uses will be apparent to one of ordinary skill in the art.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention further provides efficient methods of identifying pharmacological agents or lead compounds for agents active at the level of a SAP or SAP fragment modulatable cellular function. In particular, such functions include TGF-β superfamily signal transduction, cyclin regulation and formation of a SAP protein complex. Generally, the screening methods involve assaying for compounds which interfere with a SAP activity such as Smad binding, etc, although compounds which enhance SAP activity also can be assayed using the screening methods. Such methods are adaptable to automated, high throughput screening of compounds. The target therapeutic indications for pharmacological agents detected by the screening methods are limited only in that the target cellular function be subject to modulation by alteration of the formation of a complex comprising a SAP polypeptide or fragment thereof and one or more natural SAP intracellular binding targets, such as Smad6. Target indications include cellular processes modulated by TGF-β superfamily signal transduction following receptor-ligand binding.

A wide variety of assays for pharmacological agents are provided, including, labeled in vitro protein-protein binding assays, electrophoretic mobility shift assays, immunoassays, cell-based assays such as two- or three-hybrid screens, expression assays, etc. For example, three-hybrid screens are used to rapidly examine the effect of transfected nucleic acids on the intracellular binding of SAP or SAP fragments to specific intracellular targets. The transfected nucleic acids can encode, for example, combinatorial peptide libraries or antisense molecules. Convenient reagents for such assays, e.g., GAL4 fusion proteins, are known in the art. An exemplary cell-based assay involves transfecting a cell with a nucleic acid encoding a SAP polypeptide fused to a GAL4 DNA binding domain and a nucleic acid encoding a Smad domain which interacts with SAP fused to a transcription activation domain such as VP16. The cell also contains a reporter gene operably linked to a gene expression regulatory region, such as one or more GAL4 binding sites. Activation of reporter gene transcription occurs when the SAP and Smad fusion polypeptides bind such that the GAL4 DNA binding domain and the VP 16 transcriptional activation domain are brought into proximity to enable transcription of the reporter gene. Agents which modulate a SAP polypeptide mediated cell function are then detected through a change in the expression of reporter gene. Methods for determining changes in the expression of a reporter gene are known in the art.

SAP fragments used in the methods, when not produced by a transfected nucleic acid are added to an assay mixture as an isolated polypeptide. SAP polypeptides preferably are produced recombinantly, although such polypeptides may be isolated from biological extracts. Recombinantly produced SAP polypeptides include chimeric proteins comprising a fusion of a SAP protein with another polypeptide, e.g., a polypeptide capable of providing or enhancing protein-protein binding, sequence specific nucleic acid binding (such as GAL4), enhancing stability of the SAP polypeptide under assay conditions, or providing a detectable moiety, such as green fluorescent protein or Flag epitope as provided in the examples below.

The assay mixture is comprised of a natural intracellular SAP binding target such as Smad6 or a fragment thereof capable of interacting with SAP. While natural SAP binding targets may be used, it is frequently preferred to use portions (e.g., peptides or nucleic acid fragments) or analogs (i.e., agents which mimic the SAP binding properties of the natural binding target for purposes of the assay) of the SAP binding target so long as the portion or analog provides binding affinity and avidity to the SAP fragment measurable in the assay.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate pharmacological agent, the SAP polypeptide specifically binds the cellular binding target, a portion thereof or analog thereof. The order of addition of components, incubation temperature, time of incubation, and other perimeters of the assay ay be readily determined. Such experimentation merely involves optimization of the assay parameters, not the fundamental composition of the assay. Incubation temperatures typically re between 4° C. and 40° C. Incubation times preferably are minimized to facilitate rapid, high throughput screening, and typically are between 0.1 and 10 hours.

After incubation, the presence or absence of specific binding between the SAP polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of SAP polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a SAP binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides SAP-specific binding agents, methods of identifying and making such agents, and their use in diagnosis, therapy and pharmaceutical development. For example, SAP-specific pharmacological agents are useful in a variety of diagnostic and therapeutic applications, especially where disease or disease prognosis is associated with improper utilization of a pathway involving SAP, e.g., TGF-β receptor-Smad complex formation, TGF-β superfamily signaling, cyclin regulation of the cell cycle, etc. Novel SAP-specific binding agents include SAP-specific antibodies and other natural intracellular binding agents identified with assays such as two hybrid screens, and non-natural intracellular binding agents identified in screens of chemical libraries and the like.

In general, the specificity of SAP binding to a binding agent is shown by binding equilibrium constants. Targets which are capable of selectively binding a SAP polypeptide preferably have binding equilibrium constants of at least about $10^7$ $M^{-1}$, more preferably at least about $10^8$ $M^{-1}$, and most preferably at least about $10^9$ $M^{-1}$. The wide variety of cell based and cell free assays may be used to demonstrate SAP-specific binding. Cell based assays include one, two and three hybrid screens, assays in which SAP-mediated transcription is inhibited or increased, etc. Cell free assays include SAP-protein binding assays, immunoassays, etc. Other assays useful for screening agents which bind SAP polypeptides include fluorescence resonance energy transfer (FRET), and electrophoretic mobility shift analysis (EMSA).

Various techniques may be employed for introducing nucleic acids of the invention into cells, depending on whether the nucleic acids are introduced in vitro or in vivo in a host. Such techniques include transfection of nucleic acid-CaPO$_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

The compositions of the invention are administered in effective amounts. An "effective amount" is that amount of a composition that alone, or together with further doses, produces the desired response, e.g. alters favorably the signal transduction resulting from binding of a TGF-β superfamily ligand to specific receptors. In the case of treating a particular disease, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of SAP or nucleic acid encoding SAP for producing the desired response in a unit of weight or volume suitable for administration to a patient. The response can, for example, be measured by determining the signal transduction enhanced or inhibited by the SAP composition via a reporter system as described herein, by measuring downstream effects such as gene expression, or by measuring the physiological effects of the SAP composition, such as regression of a tumor or decrease of disease symptoms. Likewise, the effects of antisense SAP molecules can be readily determined by measuring expression of the individual genes in cells to which an antisense composition is added. Other assays will be known to one of ordinary skill in the art and can be employed for measuring the level of the response.

The doses of SAP polypeptide or nucleic acid administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of SAP are formulated and administered in doses between 1 ng and 1 mg, and preferably between 10 ng and 100 μg, according to any standard procedure in the art. Where nucleic acids encoding SAP of variants thereof are employed, doses of between 1 ng and 0.1 mg generally will be formulated and administered according to standard procedures. Other protocols for the administration of SAP compositions will be known to one of ordinary skill in the art, in which the dose amount, schedule of injections, sites of injections, mode of administration (e.g., intra-tumoral) and the like vary from the foregoing. Administration of SAP compositions to mammals other than humans, e.g. for testing purposes or veterinary therapeutic purposes, is carried out under substantially the same conditions as described above.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

SAPs may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation of SAP polypeptides or nucleic acids, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

In another aspect of the invention, SAP polypeptides or nucleic acid are used in the manufacture of a medicament for modulating a TGF-β superfamily ligand response. The medicament can be placed in a vial and be incorporated into a kit to be used for increasing a subject's response to one or more TGF-β family members. In certain embodiments, other medicaments which modulate the same responses or which favorably affect the SAP compositions can also be included in the same kit. The kits can include instructions or other printed material on how to administer the SAP compositions and any other components of the kit.

Examples

Materials and Methods

DNA Constructs pEG-Smad6S, pEG-Smad6SN, pEG-Smad6SC, pEG-Smad7, pEG-Smad7N and pEG-Smad7C were made by PCR and inserted into pEG202 (Golemis et al., Analysis of protein interactions. p. 20.1.1–20.1.40 In F. M. Ausubel, R. Brent, R. E. Kingston, D. D. Moore, J. G. Seidman, J. A. Smith and K. Struhl (eds.), Current Protocols in Molecular Biology, vol. 3, John Wiley & Sons, Inc., 1999). pEG-Smad2 and pEG-Smad4 was obtained from Dr. R. Derynk (Wu et al., *Mol. Cell. Biol.* 17:2521–2528., 1997). 6xMyc-Smad1, 6xMyc-Smad2 and 6xMyc-Smad3 were provided by Dr. K. Miyazono (Nishihara et al., *Genes. Cells*. 3:613–623, 1998). 6xMyc-Smad4, 6xMyc-Smad6S, 6xMyc-Smad6L and 6xMyc-Smad7 were constructed using 6xMyc-pcDNA3 (Nishihara et al., 1998). Flag-AMSH, Flag-AMSH(DBS2), Flag-AMSH(DBS3), Flag-AMSH (DC2), Flag-AMSH(DJS), Flag-AMSH(DNL) were described previously (Tanaka et al., *J. Biol. Chem.* 274:19129–19135, 1999). Flag-AMSH(Δ102–233), Flag-AMSH(106–424) and Flag-AMSH(234–424) were generated by PCR and subcloned into pCMV2-Flag vector (Sigma).

Yeast Two-hybrid Screening Several constructs of LexA-Smad fusions in the pEG202 vector and human fetal brain library in the pJG4–5 vector were used. Library screens were carried out using Leu2 and β-galactosidase reporters (pSH18–34) within the yeast strain, EGY48. In brief, EGY48 cells were transformed with pEG-Smad6SN, pSH18–34 and library and plated in galactose-containing medium without histidine. Positive colonies were picked 3–5 days after plating (Golemis et al., 1999). Subsequently, positive colonies were tested again and confirmed as real positive clones.

DNA Sequence Analysis

The nucleotide sequences were determined for both strands with an ABI310 DNA sequencer.

Immunoprecipitation and Western Blotting

Combinations of Smads and AMSH or its mutants in the presence or absence of ALK5ca or ALK6ca were transfected in COS7 cells at $1.2 \times 10^6$ cells/10 cm-dish using Fugene 6

(Boehringer Mannheim). Forty hours after transfection, the cells were lysed in 1 ml of lysis buffer (20 mM Tris [pH7.4], 150 mM NaCl, 10% glycerol, 1% Triton X-100, 1 mM PMSF and 100 units/ml Trasylol). The cell lysates were precleared with protein G-Sepharose beads (Pharmacia) and incubated with Flag M5 antibody (Sigma) for 2 h at 4° C. Subsequently, protein G-Sepharose beads were added to the reaction mixture and samples were incubated for 30 min at 4° C. After washing the immunoprecipitates with lysis buffer three times, immunoprecipitates and aliquots of cell lysates before immunoprecipitation were separated by SDS-polyacrylamide gel electrophoresis and transferred to a Hybond-C extra membrane (Amersham). The membrane was then probed with Flag M5 or Myc (9E10 monoclonal antibody; Santa Cruz) antibody. Primary antibodies were detected with a horseradish peroxidase-conjugated goat anti-mouse antibody (Amersham) and a chemiluminescent substrate.

[$^{32}$P]Orthophosphate Labeling of Cells, Tryptic Phosphopeptide Mapping and Two-dimensional Phosphoamino Acid Analysis COS7 cells were labeled in phosphate-free medium for 3 h. Subsequently, 1 mCi/ml [$^{32}$P]orthophosphate was added in the culture medium. After 40 min, the cells were lysed, immunoprecipitated with anti-FlagM5 antibody, separated by SDS-polyacrylamide gel electrophoresis and transferred to a Hybond-C extra membrane. For tryptic phosphopeptide mapping, AMSH bands were localized by exposure on a FujiX Bio-Imager (Fuji), excised from the filter and digested in situ with trypsin (modified sequencing grade; Promega). Two-dimensional phosphopeptide mapping was done using the Hunter thin-layer electrophoresis apparatus (HTLE-7000; CBS Scientific), essentially as described by Boyle et al. (*Methods Enzymol.* 201:110–149, 1991). First dimension electrophoresis was performed in pH 1.9 buffer (formic acid:glacial acetic acid:water; 44:156:1800) for 23 min at 2000 V, and second dimension ascending thin-layer chromatography in isobutyric acid buffer (isobutyric acid:n-butanol:pyridine:glacial acetic acid:water; 1250:38:96:58:558). After exposure, phosphopeptides were eluted from the plates in the pH 1.9 buffer and lyophilized. The fractions were then subjected to two-dimensional phosphoamino acid analysis.

Example 1: Isolation of Smad Associating Proteins

To explore further the mode of actions of Smad6 and Smad7, proteins that interact with Smad6 and Smad7 have been isolated using the yeast two hybrid system.

Figure 3:
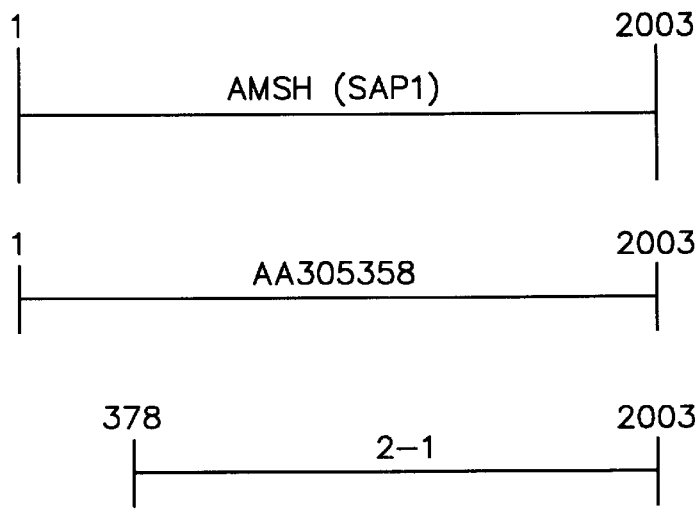
FIG. 3 depicts a map of isolated AMSH (SAP1) clones.
Figure 4:
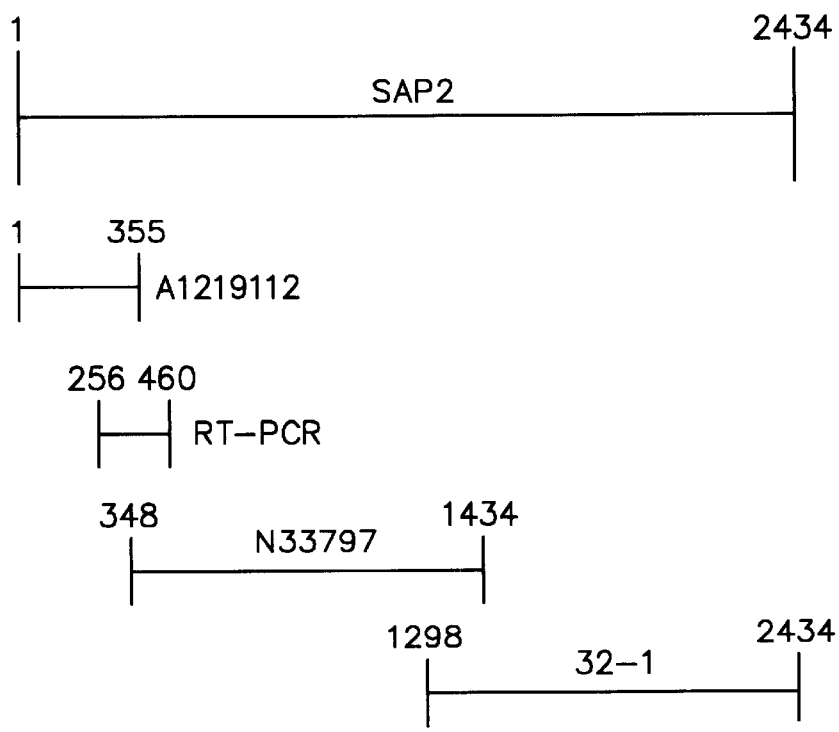
FIG. 4 shows a map of isolated SAP2 clones.

Using the N-terminal half of Smad6 MH2 domain (pEG-Smad6SN) (FIG. 1) as a bait to screen a human fetal brain library (4×10$^6$ colonies), 12 kinds of distinct positive cDNA clones encoding 7 known and 5 unknown proteins were obtained; the latter molecules were termed Smad6 associating proteins (SAPs) 1 through 5 (FIG. 2). Subsequently, the interaction of identified molecules with Smad2, Smad4, Smad6 or Smad7 was investigated using the yeast two hybrid system. As seen in FIG. 2, all clones except for dodecenoyl-CoA could bind to either Smad6S or Smad7. However, no or very weak interactions between Smad2 or Smad4 and the identified molecules were seen. Among the novel cDNAs, SAPs 1–3 were further analyzed, of which multiple positive clones were isolated (FIG. 2). The entire coding sequences for SAP1 (FIG. 3 and SEQ ID NO:1) and SAP2 (FIG. 4 and SEQ ID NO:3) were obtained as expressed sequence tags (ESTs), but no ESTs encoding SAP3 (SEQ ID NO:5) could be found.

SAP1 was previously isolated and termed "associated molecule with the SH3 domain of STAM" (AMSH) (Tanaka et al., 1999). Thus, SAP1 is called AMSH in the following. AMSH was originally found to interact with the signal transducing adaptor molecule (STAM). AMSH has three unique motifs in its structure, i.e., a nuclear translocational signal, an SH3 binding site (SXXP; SEQ ID NO:7) and a JAB1 subdomain homologous region (JSH) (FIG. 5).

In order to investigate whether AMSH interacts with Smads in vivo, COS7 cells were transfected with Flag-tagged AMSH and different Myc-tagged-Smads (Smad1, Smad4, Smad6S, Smad6L and Smad7) in the absence and presence of constitutively active ALK6 (ALK6ca). Samples were then subjected to immunoprecipitation with Flag antibodies and blotting with Myc antibodies. AMSH interacted with Smad4, Smad6S and Smad6L weakly in the absence of constitutively activate ALK6 in COS7 cells. Interestingly, upon transfection with constitutively active ALK6 the interaction of AMSH with Smad4, Smad6S and Smad6L increased. Smad7 constitutively bound to AMSH. However, Smad1 did not associate with AMSH.

In a similar experiment, ALK5-dependent interaction of AMSH was explored. COS7 cells were transfected with Flag-tagged AMSH and different Myc-tagged Smads (Smad2, Smad3, Smad4, Smad6S, Smad6L and Smad7) in the absence and presence of constitutively activated ALK5. Interestingly, activated ALK5 (ALK5ca) promoted the interaction of AMSH with Smad2 and in particular Smad3, while Smad4, Smad6S, Smad6L and Smad7 interact with AMSH independent of ALK5.

It is known that Smad6 inhibits the BMP pathway more efficiently than the TGF-β pathway (Hata et al., *Genes Devel.* 12:186–197, 1998). Since BMP receptors possess an intrinsic serine/threonine kinase, it was examined whether or not AMSH was phosphorylated, and it was determined that AMSH was phosphorylated by activated ALK6. However, AMSH might not be a direct substrate for the serine/threonine kinase of ALK6 because the phosphorylation of AMSH was detected 4 h after the treatment with OP-1 in COS7 cells which were reconstituted with AMSH, ALK6 and BMPR-II.

TGF-β family signaling has been known to be mediated in part through MAP kinase pathways (Atfi et al., *J. Biol. Chem.* 272:1429–1432, 1997; Sano et al., *J. Biol. Chem.* 274:8949–8957, 1999). Therefore, the effect of MAP kinase inhibitors was investigated on the phosphorylation of AMSH. Cells were incubated with inhibitors 3 h before the addition of [$^{32}$P]orthophosphate, SB203580, a p38 inhibitor, inhibited the phosphorylation of AMSH in a dose-dependent manner, whereas PD98059, an ERK inhibitor, had no effect. The effect of the third MAP kinase pathway, JNK, on the phosphorylation of AMSH was not investigated because no commercial inhibitor is available. The MAP kinases that mainly contribute to the phosphorylation of AMSH are confirmed using dominant negative JNK and p38 in phosphorylation experiments as described above.

Often, the phosphorylation status of a protein correlates within biological activity. Thus, tryptic phosphopeptide mapping of AMSH stimulated with ALK6ca we preformed was performed. Four major phosphopeptides were induced by ALK6ca. Phosphoamino acid analysis revealed that only serine residues were phosphorylated. The exact position of the phosphorylated serine residues in the phosphopeptides is identified by, e.g., amino acid sequencing of the phosphopeptides.

Deletion mutants of AMSH were made to find important regions for biological activity (FIG. 5). The in vivo interaction with Smad6L was investigated for two of the mutants which were found to associate with Smad6L in the presence of active ALK6. In particular, AMSH(DC2) which lacks the C-terminal half of AMSH interacted with Smad6L interacted more efficiently with Smad6L in the presence of ALK6ca. Repetition of the same experiment using all mutants depicted in FIG. 5 is performed to identify portions of AMSH which interact with Smad6 and Smad7.

The phosphorylation of AMSH mutants by ALK6ca was tested as well. AMSH(DBS2) was highly phosphorylated. On the other hand, the phosphorylation of AMSH(DC2) was very weak. These observations suggest that the N-terminal part of AMSH is involved in the interaction with Smad6L, whereas phosphorylation sites are localized in the C-terminal part. The phosphorylation of other mutants depicted in FIG. 5 by ALK6ca also is performed to confirm results and further localize phosphorylation sites.

The effect of AMSH and mutants thereof are tested in a luciferase assay for TGF-β-family-dependent activity (e.g., Jonk et al., *J. Biol. Chem.* 273:21145–21152, 1998) as well as for their effect in a Xenopus animal cap assay (e.g., Nakao et al., *Nature* 389:631–635, 1997).

A Xenopus homologue of SAP2 was recently identified and termed XDRP 1. (GenBank accession number AB030502; Funakoshi et al., *EMBO J.* 18:5009–5018, 1999). It was reported that XDRP1 binds to cyclin A and inhibits its degradation. Since cyclin A is involved in the cell cycle, it is possible that Smad6L regulates the cell cycle through the interaction with SAP2. Alternatively, SAP2 may regulate the degradation of Smad6L.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule selected from the group consisting of
   (a) nucleic acid molecules which hybridize under stringent conditions to a molecule consisting of the nucleic acid sequence set forth in SEQ ID NO:3 and which code for a polypeptide which binds Smad6, wherein the stringent conditions are hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS 2 mM EDTA). SSC, is 0.15M sodium chloride/0.015M sodium citrate, pH7; SDS is sodium dodecyl sulphate; and EDTA is ethylenediaminetetracetic acid,
   (b) nucleic acid molecules that differ from the nucleic acid molecules of (a) in codon sequence due to the degeneracy of the genetic code, and
   (c) complements of (a) and (b).

2. The isolated nucleic acid molecule of claim 1, wherein the isolated nucleic acid molecule consists of SEQ ID NO:3.

3. An expression vector comprising the isolated nucleic acid molecule of claim 1 operably linked to a promoter.

4. A host cell transformed or transfected with the expression vector of claim 3.

5. A method for producing a polypeptide comprising culturing the host cell of claim 4 under conditions which permit the expression of polypeptide.

6. The method of claim 5, further comprising isolating the polypeptide.

7. The isolated nucleic acid molecule of claim 1, wherein the isolated nucleic acid molecule comprises SEQ ID NO:3.

8. An expression vector comprising the isolated nucleic acid molecule of claim 7 operably linked to a promoter.

9. A host cell transformed or transfected with the expression vector of claim 8.

10. A method for producing a polypeptide comprising culturing the host cell of claim 9 under conditions which permit the expression of polypeptide.

11. The method of claim 10, further comprising isolating the polypeptide.

12. An isolated nucleic acid molecule selected from the group consisting of (a) a fragment of nucleotides 1–2399 of SEQ ID NO:3 between 12 and 2398 nucleotides in length that codes for a polypeptide that binds Smad6, and (b) complements of "(a)", provided that the nucleic acid molecule excludes sequences consisting of SEQ ID NO:17, SEQ ID NO:18 and SEQ ID NO:19.

13. The isolated nucleic acid molecule of claim 12, wherein the isolated nucleic acid molecule comprises at least 22 contiguous nucleotides.

14. The isolated nucleic acid molecule of claim 12, wherein the isolated nucleic acid molecule comprises at least 25 contiguous nucleotides.

15. The isolated nucleic acid molecule of claim 12, wherein the isolated nucleic acid molecule comprises at least 30 contiguous nucleotides.

16. The isolated nucleic acid molecule of claim 12, wherein the isolated nucleic acid molecule comprises at least 40 contiguous nucleotides.

17. The isolated nucleic acid molecule of claim 12, wherein the isolated nucleic acid molecule comprises at least 50 contiguous nucleotides.

18. The isolated nucleic acid molecule of claim 12, wherein the isolated nucleic acid molecule comprises at least 75 contiguous nucleotides.

19. The isolated nucleic acid molecule of claim 12, wherein the isolated nucleic acid molecule comprises at least 100 contiguous nucleotides.

20. The isolated nucleic acid molecule of claim 12, wherein the isolated nucleic acid molecule comprises between 20 and 32 contiguous nucleotides.

* * * * *

SEQUENCE LISTING

<160> NUMBER OF SEQ ID NOS: 20

<210> SEQ ID NO 1
<211> LENGTH: 2003
<212> TYPE: DNA
<213> ORGANISM: Homo sapiens
<220> FEATURE:
<221> NAME/KEY: CDS
<222> LOCATION: (63)..(1334)

<400> SEQUENCE: 1

```
gaattcggca cgaggtttcc ggaacctccg ggtgtcatcc gcggggaaag aacttggtcc       60 tg atg tct gac cat gga gat gtg agc ctc ccg ccc gaa gac cgg gtg      107
   Met Ser Asp His Gly Asp Val Ser Leu Pro Pro Glu Asp Arg Val
   1               5                  10                  15 agg gct ctc tcc cag ctg ggt agt gcg gta gag gtg aat gaa gac att      155
Arg Ala Leu Ser Gln Leu Gly Ser Ala Val Glu Val Asn Glu Asp Ile
                20                  25                  30 cca ccc cgt cgg tac ttc cgc tct gga gtt gag att atc cga atg gca      203
Pro Pro Arg Arg Tyr Phe Arg Ser Gly Val Glu Ile Ile Arg Met Ala
            35                  40                  45 tcc att tac tct gag gaa ggc aac att gaa cat gcc ttc atc ctc tat      251
Ser Ile Tyr Ser Glu Glu Gly Asn Ile Glu His Ala Phe Ile Leu Tyr
        50                  55                  60 aac aag tat atc acg ctc ttt att gag aaa cta cca aaa cat cga gat      299
Asn Lys Tyr Ile Thr Leu Phe Ile Glu Lys Leu Pro Lys His Arg Asp
    65                  70                  75 tac aaa tct gct gtc att cct gaa aag aaa gac aca gta aag aaa tta      347
Tyr Lys Ser Ala Val Ile Pro Glu Lys Lys Asp Thr Val Lys Lys Leu
80                  85                  90                  95 aag gag att gca ttt ccc aaa gca gaa gag ctg aag gca gag ctg tta      395
Lys Glu Ile Ala Phe Pro Lys Ala Glu Glu Leu Lys Ala Glu Leu Leu
                100                 105                 110 aaa cga tat acc aaa gaa tat aca gaa tat aat gaa gaa aag aag aag      443
Lys Arg Tyr Thr Lys Glu Tyr Thr Glu Tyr Asn Glu Glu Lys Lys Lys
            115                 120                 125 gaa gca gag gaa ttg gcc cgg aac atg gcc atc cag caa gag ctg gaa      491
Glu Ala Glu Glu Leu Ala Arg Asn Met Ala Ile Gln Gln Glu Leu Glu
        130                 135                 140 aag gaa aaa cag agg gta gca caa cag aag cag cag caa ttg gaa cag      539
```

```
Lys Glu Lys Gln Arg Val Ala Gln Gln Lys Gln Gln Leu Glu Gln
    145                 150                 155 gaa cag ttc cat gcc ttc gag gag atg atc cgg aac cag gag cta gaa      587
Glu Gln Phe His Ala Phe Glu Glu Met Ile Arg Asn Gln Glu Leu Glu
160                 165                 170                 175 aaa gag cga ctg aaa att gta cag gag ttt ggg aag gta gac cct ggc      635
Lys Glu Arg Leu Lys Ile Val Gln Glu Phe Gly Lys Val Asp Pro Gly
                180                 185                 190 cta ggt ggc ccg cta gtg cct gac ttg gag aag ccc tcc tta gat gtg      683
Leu Gly Gly Pro Leu Val Pro Asp Leu Glu Lys Pro Ser Leu Asp Val
            195                 200                 205 ttc ccc acc tta aca gtc tca tcc ata cag cct tca gac tgt cac aca      731
Phe Pro Thr Leu Thr Val Ser Ser Ile Gln Pro Ser Asp Cys His Thr
        210                 215                 220 act gta agg cca gct aag cca cct gtg gtg gac agg tcc ttg aaa cct      779
Thr Val Arg Pro Ala Lys Pro Pro Val Val Asp Arg Ser Leu Lys Pro
    225                 230                 235 gga gca ctg agc aac tca gaa agt att ccc aca atc gat gga ttg cgc      827
Gly Ala Leu Ser Asn Ser Glu Ser Ile Pro Thr Ile Asp Gly Leu Arg
240                 245                 250                 255 cat gtg gtg gtg cct ggg cgg ctg tgc cca cag ttt ctc cag tta gcc      875
His Val Val Val Pro Gly Arg Leu Cys Pro Gln Phe Leu Gln Leu Ala
                260                 265                 270 agt gcc aac act gcc cgg gga gtg gag aca tgt gga att ctc tgt gga      923
Ser Ala Asn Thr Ala Arg Gly Val Glu Thr Cys Gly Ile Leu Cys Gly
            275                 280                 285 aaa ctg atg agg aat gaa ttt acc att acc cat gtt ctc atc ccc aag      971
Lys Leu Met Arg Asn Glu Phe Thr Ile Thr His Val Leu Ile Pro Lys
        290                 295                 300 caa agt gct ggg tct gat tac tgc aac aca gag aac gaa gaa gaa ctt     1019
Gln Ser Ala Gly Ser Asp Tyr Cys Asn Thr Glu Asn Glu Glu Glu Leu
    305                 310                 315 ttc ctc ata cag gat cag cag ggc ctc atc aca ctg ggc tgg att cat     1067
Phe Leu Ile Gln Asp Gln Gln Gly Leu Ile Thr Leu Gly Trp Ile His
320                 325                 330                 335 act cac ccc aca cag acc gcg ttt ctc tcc agt gtc gac cta cac act     1115
Thr His Pro Thr Gln Thr Ala Phe Leu Ser Ser Val Asp Leu His Thr
                340                 345                 350 cac tgc tct tac cag atg atg ttg cca gag tca gta gcc att gtt tgc     1163
His Cys Ser Tyr Gln Met Met Leu Pro Glu Ser Val Ala Ile Val Cys
            355                 360                 365 tcc ccc aag ttc cag gaa act gga ttc ttt aaa cta act gac cat gga     1211
Ser Pro Lys Phe Gln Glu Thr Gly Phe Phe Lys Leu Thr Asp His Gly
        370                 375                 380 cta gag gag att tct tcc tgt cgc cag aaa gga ttt cat cca cac agc     1259
Leu Glu Glu Ile Ser Ser Cys Arg Gln Lys Gly Phe His Pro His Ser
    385                 390                 395 aag gat cca cct ctg ttc tgt agc tgc agc cac gtg act gtt gtg gac     1307
Lys Asp Pro Pro Leu Phe Cys Ser Cys Ser His Val Thr Val Val Asp
400                 405                 410                 415 aga gca gtg acc atc aca gac ctt cga tgagcgtttg agtccaacac           1354
Arg Ala Val Thr Ile Thr Asp Leu Arg
                420 cttccaagaa caacaaaacc atatcagtgt actgtagccc cttaatttaa gctttctaga   1414 aagctttgga agttttgta gatagtagaa aggggggcat cacctgagaa agagctgatt    1474 ttgtatttca ggtttgaaaa gaaataactg aacatatttt ttaggcaagt cagaaagaga   1534 acatggtcac ccaaaagcaa ctgtaactca gaaattaagt tactcagaaa ttaagtagct   1594 cagaaattaa gaaagaatgg tataatgaac ccccatatac ccttccttct ggattcacca   1654
```

-continued

```
attgttaaca tttttttcct ctcagctatc cttctaattt ctctctaatt tcaatttgtt   1714
tatatttacc tctgggctca ataagggcat ctgtgcagaa atttggaagc catttagaaa   1774
atcttttgga ttttcctgtg gtttatggca atatgaatgg agcttattac tggggtgagg   1834
gacagcttac tccatttgac cagattgttt ggctaacaca tcccgaagaa tgattttgtc   1894
aggaattatt gttatttaat aaatatttca ggatattttt cctctacaat aaagtaacaa   1954
ttaacttaaa aaaaaaaaaa aaaaaaaaaa aaaaaaaaaa aaactcgag               2003
```

<210> SEQ ID NO 2
<211> LENGTH: 424
<212> TYPE: PRT
<213> ORGANISM: Homo sapiens

<400> SEQUENCE: 2

| Met | Ser | Asp | His | Gly | Asp | Val | Ser | Leu | Pro | Pro | Glu | Asp | Arg | Val | Arg |
|---|---|---|---|---|---|---|---|---|---|---|---|---|---|---|---|
| 1 | | | | 5 | | | | | 10 | | | | | 15 | |

Ala Leu Ser Gln Leu Gly Ser Ala Val Glu Val Asn Glu Asp Ile Pro
                20                  25                  30

Pro Arg Arg Tyr Phe Arg Ser Gly Val Glu Ile Ile Arg Met Ala Ser
            35                  40                  45

Ile Tyr Ser Glu Glu Gly Asn Ile Glu His Ala Phe Ile Leu Tyr Asn
    50                  55                  60

Lys Tyr Ile Thr Leu Phe Ile Glu Lys Leu Pro Lys His Arg Asp Tyr
65                  70                  75                  80

Lys Ser Ala Val Ile Pro Glu Lys Lys Asp Thr Val Lys Lys Leu Lys
                85                  90                  95

Glu Ile Ala Phe Pro Lys Ala Glu Glu Leu Lys Ala Glu Leu Leu Lys
            100                 105                 110

Arg Tyr Thr Lys Glu Tyr Thr Glu Tyr Asn Glu Glu Lys Lys Lys Glu
        115                 120                 125

Ala Glu Glu Leu Ala Arg Asn Met Ala Ile Gln Gln Glu Leu Glu Lys
    130                 135                 140

Glu Lys Gln Arg Val Ala Gln Gln Lys Gln Gln Gln Leu Glu Gln Glu
145                 150                 155                 160

Gln Phe His Ala Phe Glu Glu Met Ile Arg Asn Gln Glu Leu Glu Lys
                165                 170                 175

Glu Arg Leu Lys Ile Val Gln Glu Phe Gly Lys Val Asp Pro Gly Leu
            180                 185                 190

Gly Gly Pro Leu Val Pro Asp Leu Glu Lys Pro Ser Leu Asp Val Phe
        195                 200                 205

Pro Thr Leu Thr Val Ser Ser Ile Gln Pro Ser Asp Cys His Thr Thr
    210                 215                 220

Val Arg Pro Ala Lys Pro Pro Val Asp Arg Ser Leu Lys Pro Gly
225                 230                 235                 240

Ala Leu Ser Asn Ser Glu Ser Ile Pro Thr Ile Asp Gly Leu Arg His
                245                 250                 255

Val Val Val Pro Gly Arg Leu Cys Pro Gln Phe Leu Gln Leu Ala Ser
            260                 265                 270

Ala Asn Thr Ala Arg Gly Val Glu Thr Cys Gly Ile Leu Cys Gly Lys
        275                 280                 285

Leu Met Arg Asn Glu Phe Thr Ile Thr His Val Leu Ile Pro Lys Gln
    290                 295                 300

Ser Ala Gly Ser Asp Tyr Cys Asn Thr Glu Asn Glu Glu Glu Leu Phe

-continued

```
            305                 310                 315                 320
Leu Ile Gln Asp Gln Gln Gly Leu Ile Thr Leu Gly Trp Ile His Thr
                325                 330                 335

His Pro Thr Gln Thr Ala Phe Leu Ser Ser Val Asp Leu His Thr His
            340                 345                 350

Cys Ser Tyr Gln Met Met Leu Pro Glu Ser Val Ala Ile Val Cys Ser
            355                 360                 365

Pro Lys Phe Gln Glu Thr Gly Phe Phe Lys Leu Thr Asp His Gly Leu
        370                 375                 380

Glu Glu Ile Ser Ser Cys Arg Gln Lys Gly Phe His Pro His Ser Lys
385                 390                 395                 400

Asp Pro Pro Leu Phe Cys Ser Cys Ser His Val Thr Val Val Asp Arg
                405                 410                 415

Ala Val Thr Ile Thr Asp Leu Arg
                420

<210> SEQ ID NO 3
<211> LENGTH: 2434
<212> TYPE: DNA
<213> ORGANISM: Homo sapiens
<220> FEATURE:
<221> NAME/KEY: CDS
<222> LOCATION: (270)..(2036)

<400> SEQUENCE: 3
aagcggtggc tgctgcggat gtcggtgtga gcgagcggcg cctgaacaca cggcggctgc      60
cgagcgcctg acccgggcct gcgccagagc ctgcaccgag ctccggggcc ccacacccgc     120
taccgtggcc ctgcgcccgt tgctactgag gcggcgtgct ctgcattctt cgctgtccag     180
gcctgccggc tctggtgtct gctggctcct ccttgctcgc ctgctccctc ctgcttgcct     240
gagtcaccgc cgccgccgcc gccacagcc atg gcc gag agt ggt gaa agc ggc       293
                                 Met Ala Glu Ser Gly Glu Ser Gly
                                  1               5 ggt cct ccg ggc tcc cag gat agc gcc gcc gga gcc gaa ggt gct ggc       341
Gly Pro Pro Gly Ser Gln Asp Ser Ala Ala Gly Ala Glu Gly Ala Gly
     10                  15                  20 gcc ccc gcg gcc gct gcc tcc gcg gag ccc aaa atc atg aaa gtc acc       389
Ala Pro Ala Ala Ala Ala Ser Ala Glu Pro Lys Ile Met Lys Val Thr
25                  30                  35                  40 gtg aag acc ccg aag gaa aag gag gaa ttc gcc gtg ccc gag aat agc       437
Val Lys Thr Pro Lys Glu Lys Glu Glu Phe Ala Val Pro Glu Asn Ser
                 45                  50                  55 tcc gtc cag cag ttt aag gaa gaa atc tct aaa cgt ttt aaa tca cat       485
Ser Val Gln Gln Phe Lys Glu Glu Ile Ser Lys Arg Phe Lys Ser His
             60                  65                  70 act gac caa ctt gtg ttg ata ttt gct gga aaa att ttg aaa gat caa       533
Thr Asp Gln Leu Val Leu Ile Phe Ala Gly Lys Ile Leu Lys Asp Gln
         75                  80                  85 gat acc ttg agt cag cat gga att cat gat gga ctt act gtt cac ctt       581
Asp Thr Leu Ser Gln His Gly Ile His Asp Gly Leu Thr Val His Leu
     90                  95                 100 gtc att aaa aca caa aac agg cct cag gat cat tca gct cag caa aca       629
Val Ile Lys Thr Gln Asn Arg Pro Gln Asp His Ser Ala Gln Gln Thr
105                 110                 115                 120 aat aca gct gga agc aat gtt act aca tca tca act cct aat agt aac       677
Asn Thr Ala Gly Ser Asn Val Thr Thr Ser Ser Thr Pro Asn Ser Asn
                125                 130                 135 tct aca tct ggt tct gct act agc aac cct ttt ggt tta ggt ggc ctt       725
```

```
                -continued

Ser Thr Ser Gly Ser Ala Thr Ser Asn Pro Phe Gly Leu Gly Gly Leu
            140                 145                 150 ggg gga ctt gca ggt ctg agt agc ttg ggt ttg aat act acc aac ttc      773
Gly Gly Leu Ala Gly Leu Ser Ser Leu Gly Leu Asn Thr Thr Asn Phe
            155                 160                 165 tct gaa cta cag agt cag atg cag cga caa ctt ttg tct aac cct gaa      821
Ser Glu Leu Gln Ser Gln Met Gln Arg Gln Leu Leu Ser Asn Pro Glu
            170                 175                 180 atg atg gtc cag atc atg gaa aat ccc ttt gtt cag agc atg ctc tca      869
Met Met Val Gln Ile Met Glu Asn Pro Phe Val Gln Ser Met Leu Ser
185                 190                 195                 200 aat cct gac ctg atg aga cag tta att atg gcc aat cca caa atg cag      917
Asn Pro Asp Leu Met Arg Gln Leu Ile Met Ala Asn Pro Gln Met Gln
            205                 210                 215 cag ttg ata cag aga aat cca gaa att agt cat atg ttg aat aat cca      965
Gln Leu Ile Gln Arg Asn Pro Glu Ile Ser His Met Leu Asn Asn Pro
            220                 225                 230 gat ata atg aga caa acg ttg gaa ctt gcc agg aat cca gca atg atg     1013
Asp Ile Met Arg Gln Thr Leu Glu Leu Ala Arg Asn Pro Ala Met Met
            235                 240                 245 cag gag atg atg agg aac cag gac cga gct ttg agc aac cta gaa agc     1061
Gln Glu Met Met Arg Asn Gln Asp Arg Ala Leu Ser Asn Leu Glu Ser
250                 255                 260 atc cca ggg gga tat aat gct tta agg cgc atg tac aca gat att cag     1109
Ile Pro Gly Gly Tyr Asn Ala Leu Arg Arg Met Tyr Thr Asp Ile Gln
265                 270                 275                 280 gaa cca atg ctg agt gct gca caa gag cag ttt ggt ggt aat cca ttt     1157
Glu Pro Met Leu Ser Ala Ala Gln Glu Gln Phe Gly Gly Asn Pro Phe
            285                 290                 295 gct tcc ttg gtg agc aat aca tcc tct ggt gaa ggt agt caa cct tcc     1205
Ala Ser Leu Val Ser Asn Thr Ser Ser Gly Glu Gly Ser Gln Pro Ser
            300                 305                 310 cgt aca gaa aat aga gat cca cta ccc aat cca tgg gct cca cag act     1253
Arg Thr Glu Asn Arg Asp Pro Leu Pro Asn Pro Trp Ala Pro Gln Thr
            315                 320                 325 tcc cag agt tca tca gct tcc agc ggc act gcc agc act gtg ggt ggc     1301
Ser Gln Ser Ser Ser Ala Ser Ser Gly Thr Ala Ser Thr Val Gly Gly
            330                 335                 340 act act ggt agt act gcc agt ggc act tct ggg cag agt act act gcg     1349
Thr Thr Gly Ser Thr Ala Ser Gly Thr Ser Gly Gln Ser Thr Thr Ala
345                 350                 355                 360 cca aat ttg gtg cct gga gta gga gct agt atg ttc aac aca cca gga     1397
Pro Asn Leu Val Pro Gly Val Gly Ala Ser Met Phe Asn Thr Pro Gly
            365                 370                 375 atg cag agc ttg ttg caa caa ata act gaa aac cca caa ctg atg caa     1445
Met Gln Ser Leu Leu Gln Gln Ile Thr Glu Asn Pro Gln Leu Met Gln
            380                 385                 390 aac atg ttg tct gcc ccc tac atg aga agc atg atg cag tca cta agc     1493
Asn Met Leu Ser Ala Pro Tyr Met Arg Ser Met Met Gln Ser Leu Ser
            395                 400                 405 cag aat cct gac ctt gct gca cag atg atg ctg aat aat ccc cta ttt     1541
Gln Asn Pro Asp Leu Ala Ala Gln Met Met Leu Asn Asn Pro Leu Phe
            410                 415                 420 gct gga aat cct cag ctt caa gaa caa atg aga caa cag ctc cca act     1589
Ala Gly Asn Pro Gln Leu Gln Glu Gln Met Arg Gln Gln Leu Pro Thr
425                 430                 435                 440 ttc ctc caa caa atg cag aat cct gat aca cta tca gca atg tca aac     1637
Phe Leu Gln Gln Met Gln Asn Pro Asp Thr Leu Ser Ala Met Ser Asn
            445                 450                 455
```

-continued

```
cct aga gca atg cag gcc ttg tta cag att cag cag ggt tta cag aca      1685
Pro Arg Ala Met Gln Ala Leu Leu Gln Ile Gln Gln Gly Leu Gln Thr
        460                 465                 470 tta gca acg gaa gcc ccg ggc ctc atc cca ggg ttt act cct ggc ttg      1733
Leu Ala Thr Glu Ala Pro Gly Leu Ile Pro Gly Phe Thr Pro Gly Leu
            475                 480                 485 ggg gca tta gga agc act gga ggc tct tcg gga act aat gga tct aac      1781
Gly Ala Leu Gly Ser Thr Gly Gly Ser Ser Gly Thr Asn Gly Ser Asn
        490                 495                 500 gcc aca cct agt gaa aac aca agt ccc aca gca gga acc act gaa cct      1829
Ala Thr Pro Ser Glu Asn Thr Ser Pro Thr Ala Gly Thr Thr Glu Pro
505                 510                 515                 520 gga cat cag cag ttt att cag cag atg ctg cag gct ctt gct gga gta      1877
Gly His Gln Gln Phe Ile Gln Gln Met Leu Gln Ala Leu Ala Gly Val
                525                 530                 535 aat cct cag cta cag aat cca gaa gtc aga ttt cag caa caa ctg gaa      1925
Asn Pro Gln Leu Gln Asn Pro Glu Val Arg Phe Gln Gln Gln Leu Glu
            540                 545                 550 caa ctc agt gca atg gga ttt ttg aac cgt gaa gca aac ttg caa gct      1973
Gln Leu Ser Ala Met Gly Phe Leu Asn Arg Glu Ala Asn Leu Gln Ala
        555                 560                 565 cta ata gca aca gga ggt gat atc aat gca gct att gaa agg tta ctg      2021
Leu Ile Ala Thr Gly Gly Asp Ile Asn Ala Ala Ile Glu Arg Leu Leu
570                 575                 580 ggc tcc cag cca tca tagcagcatt tctgtatctt gaaaaatgt aatttatttt      2076
Gly Ser Gln Pro Ser
585 tgataacggc tcttaaactt taaaatacct gctttattc attttgactc ttggaattct    2136 gtgctgttat aaacaaaccc aatatgatgc attttaaggt ggagtacagt aagatgtgtg    2196 ggttttctg tattttctt ttctggaaca gtgggaatta aggctactgc atgcatcact     2256 tctgcattta ttgtaatttt ttaaaaacat cacctttat agttgggtga ccagattttg    2316 tcctgcatct gtccagttta tttgctttt aaacattagc ctatggtagt aatttatgta    2376 gaataaaagc attaaaaaga agcaaaaaaa aaaaaaaaa aaaaaaaaaa aactcgag      2434
```

<210> SEQ ID NO 4
<211> LENGTH: 589
<212> TYPE: PRT
<213> ORGANISM: Homo sapiens

<400> SEQUENCE: 4

```
Met Ala Glu Ser Gly Glu Ser Gly Gly Pro Gly Ser Gln Asp Ser
1               5                   10                  15

Ala Ala Gly Ala Glu Gly Ala Gly Ala Pro Ala Ala Ala Ser Ala
            20                  25                  30

Glu Pro Lys Ile Met Lys Val Thr Val Lys Thr Pro Lys Glu Lys Glu
        35                  40                  45

Glu Phe Ala Val Pro Glu Asn Ser Ser Val Gln Gln Phe Lys Glu Glu
    50                  55                  60

Ile Ser Lys Arg Phe Lys Ser His Thr Asp Gln Leu Val Leu Ile Phe
65                  70                  75                  80

Ala Gly Lys Ile Leu Lys Asp Gln Asp Thr Leu Ser Gln His Gly Ile
                85                  90                  95

His Asp Gly Leu Thr Val His Leu Val Ile Lys Thr Gln Asn Arg Pro
            100                 105                 110

Gln Asp His Ser Ala Gln Gln Thr Asn Thr Ala Gly Ser Asn Val Thr
        115                 120                 125
```

-continued

```
Thr Ser Ser Thr Pro Asn Ser Asn Ser Thr Ser Gly Ser Ala Thr Ser
    130                 135                 140

Asn Pro Phe Gly Leu Gly Gly Leu Gly Gly Leu Ala Gly Leu Ser Ser
145                 150                 155                 160

Leu Gly Leu Asn Thr Thr Asn Phe Ser Glu Leu Gln Ser Gln Met Gln
            165                 170                 175

Arg Gln Leu Leu Ser Asn Pro Glu Met Met Val Gln Ile Met Glu Asn
                180                 185                 190

Pro Phe Val Gln Ser Met Leu Ser Asn Pro Asp Leu Met Arg Gln Leu
            195                 200                 205

Ile Met Ala Asn Pro Gln Met Gln Gln Leu Ile Gln Arg Asn Pro Glu
    210                 215                 220

Ile Ser His Met Leu Asn Asn Pro Asp Ile Met Arg Gln Thr Leu Glu
225                 230                 235                 240

Leu Ala Arg Asn Pro Ala Met Met Gln Glu Met Met Arg Asn Gln Asp
                245                 250                 255

Arg Ala Leu Ser Asn Leu Glu Ser Ile Pro Gly Gly Tyr Asn Ala Leu
            260                 265                 270

Arg Arg Met Tyr Thr Asp Ile Gln Glu Pro Met Leu Ser Ala Ala Gln
            275                 280                 285

Glu Gln Phe Gly Gly Asn Pro Phe Ala Ser Leu Val Ser Asn Thr Ser
    290                 295                 300

Ser Gly Glu Gly Ser Gln Pro Ser Arg Thr Glu Asn Arg Asp Pro Leu
305                 310                 315                 320

Pro Asn Pro Trp Ala Pro Gln Thr Ser Gln Ser Ser Ala Ser Ser
            325                 330                 335

Gly Thr Ala Ser Thr Val Gly Gly Thr Thr Gly Ser Thr Ala Ser Gly
            340                 345                 350

Thr Ser Gly Gln Ser Thr Thr Ala Pro Asn Leu Val Pro Gly Val Gly
    355                 360                 365

Ala Ser Met Phe Asn Thr Pro Gly Met Gln Ser Leu Leu Gln Gln Ile
    370                 375                 380

Thr Glu Asn Pro Gln Leu Met Gln Asn Met Leu Ser Ala Pro Tyr Met
385                 390                 395                 400

Arg Ser Met Met Gln Ser Leu Ser Gln Asn Pro Asp Leu Ala Ala Gln
            405                 410                 415

Met Met Leu Asn Asn Pro Leu Phe Ala Gly Asn Pro Gln Leu Gln Glu
            420                 425                 430

Gln Met Arg Gln Gln Leu Pro Thr Phe Leu Gln Gln Met Gln Asn Pro
    435                 440                 445

Asp Thr Leu Ser Ala Met Ser Asn Pro Arg Ala Met Gln Ala Leu Leu
    450                 455                 460

Gln Ile Gln Gln Gly Leu Gln Thr Leu Ala Thr Glu Ala Pro Gly Leu
465                 470                 475                 480

Ile Pro Gly Phe Thr Pro Gly Leu Gly Ala Leu Gly Ser Thr Gly Gly
            485                 490                 495

Ser Ser Gly Thr Asn Gly Ser Asn Ala Thr Pro Ser Glu Asn Thr Ser
            500                 505                 510

Pro Thr Ala Gly Thr Thr Glu Pro Gly His Gln Gln Phe Ile Gln Gln
            515                 520                 525

Met Leu Gln Ala Leu Ala Gly Val Asn Pro Gln Leu Gln Asn Pro Glu
    530                 535                 540
```

```
Val Arg Phe Gln Gln Leu Glu Gln Leu Ser Ala Met Gly Phe Leu
545                 550                 555                 560

Asn Arg Glu Ala Asn Leu Gln Ala Leu Ile Ala Thr Gly Gly Asp Ile
                565                 570                 575

Asn Ala Ala Ile Glu Arg Leu Leu Gly Ser Gln Pro Ser
            580                 585

<210> SEQ ID NO 5
<211> LENGTH: 882
<212> TYPE: DNA
<213> ORGANISM: Homo sapiens
<220> FEATURE:
<221> NAME/KEY: CDS
<222> LOCATION: (1)..(630)

<400> SEQUENCE: 5
```

| | | |
|---|---|---|
| gaa ttc ggc acg agg cgc ggt ccc ccc ctc tcc ctc cgc ttc gca ctc<br>Glu Phe Gly Thr Arg Arg Gly Pro Pro Leu Ser Leu Arg Phe Ala Leu<br>1               5                   10                  15 | | 48 |
| ccg tcg ggt acg gga agg tcc aag ccg ctg ccg ggt gcc cga ggg ccg<br>Pro Ser Gly Thr Gly Arg Ser Lys Pro Leu Pro Gly Ala Arg Gly Pro<br>            20                  25                  30 | | 96 |
| tcg tgg ccg ccg tcg cca cgg gtc cca atg gag ccg ccg aat ctc tat<br>Ser Trp Pro Pro Ser Pro Arg Val Pro Met Glu Pro Pro Asn Leu Tyr<br>        35                  40                  45 | | 144 |
| ccg gtg aag ctc tac gtg tac gac ctg tcc aaa ggc ctg gcc cgg cgg<br>Pro Val Lys Leu Tyr Val Tyr Asp Leu Ser Lys Gly Leu Ala Arg Arg<br>50                  55                  60 | | 192 |
| ctc agc ccc atc atg ctg ggg aaa caa ctg gaa ggc atc tgg cac aca<br>Leu Ser Pro Ile Met Leu Gly Lys Gln Leu Glu Gly Ile Trp His Thr<br>65                  70                  75                  80 | | 240 |
| tcc ata gtt gtg cac aag gat gag ttc ttc ttc ggc agt ggt ggt atc<br>Ser Ile Val Val His Lys Asp Glu Phe Phe Phe Gly Ser Gly Gly Ile<br>                85                  90                  95 | | 288 |
| tcc agc tgc ccc ccg gga ggg aca ttg ctt ggg cct cca gac tct gtg<br>Ser Ser Cys Pro Pro Gly Gly Thr Leu Leu Gly Pro Pro Asp Ser Val<br>            100                 105                 110 | | 336 |
| gtt gat gtg ggg agt aca gaa gtc aca gaa gaa atc ttc ttc tgg agt<br>Val Asp Val Gly Ser Thr Glu Val Thr Glu Glu Ile Phe Phe Trp Ser<br>        115                 120                 125 | | 384 |
| acc tct cct ccc tgg ggg agt ccc tgt ttc cga ggt gag gcc tac aac<br>Thr Ser Pro Pro Trp Gly Ser Pro Cys Phe Arg Gly Glu Ala Tyr Asn<br>130                 135                 140 | | 432 |
| ctc ttt gaa cac aat tgt aac acc ttc agc aac gaa gtg gca cag ttc<br>Leu Phe Glu His Asn Cys Asn Thr Phe Ser Asn Glu Val Ala Gln Phe<br>145                 150                 155                 160 | | 480 |
| ctg act ggg cgg aag att cct tct tac atc aca gac ctg ccc tct gaa<br>Leu Thr Gly Arg Lys Ile Pro Ser Tyr Ile Thr Asp Leu Pro Ser Glu<br>                165                 170                 175 | | 528 |
| gtt ctc tcc acg ccc ttt gga cag gca ctt cgg ccc ctc ctg gac tcc<br>Val Leu Ser Thr Pro Phe Gly Gln Ala Leu Arg Pro Leu Leu Asp Ser<br>            180                 185                 190 | | 576 |
| att cag atc cag cct cca gga ggg agc tcc gtg ggc aga ccc aac ggc<br>Ile Gln Ile Gln Pro Pro Gly Gly Ser Ser Val Gly Arg Pro Asn Gly<br>        195                 200                 205 | | 624 |
| cag agc taacaggact gcctgggacc gccctgcctc accagggctt ttccttttta<br>Gln Ser<br>    210 | | 680 |
| aacaaaacaa accctaccag atttctattt tataatttta catcagagct aacaaccagg | | 740 |
| ggacggcttt ttaaatttcc cagggaagga gaccgtcagg ccgcatgtag acaatgctgc | | 800 |

```
taagaaacag aacaaaatgc caccccttct aatagtatta tactaattta ttaagaaaaa      860
aaaaaaaaaa aaaaaactcg ag                                               882
```

<210> SEQ ID NO 6
<211> LENGTH: 210
<212> TYPE: PRT
<213> ORGANISM: Homo sapiens

<400> SEQUENCE: 6

```
Glu Phe Gly Thr Arg Arg Gly Pro Pro Leu Ser Leu Arg Phe Ala Leu
1               5                   10                  15

Pro Ser Gly Thr Gly Arg Ser Lys Pro Leu Pro Gly Ala Arg Gly Pro
            20                  25                  30

Ser Trp Pro Pro Ser Pro Arg Val Pro Met Glu Pro Asn Leu Tyr
        35                  40                  45

Pro Val Lys Leu Tyr Val Tyr Asp Leu Ser Lys Gly Leu Ala Arg Arg
    50                  55                  60

Leu Ser Pro Ile Met Leu Gly Lys Gln Leu Glu Gly Ile Trp His Thr
65                  70                  75                  80

Ser Ile Val Val His Lys Asp Glu Phe Phe Phe Gly Ser Gly Gly Ile
                85                  90                  95

Ser Ser Cys Pro Pro Gly Gly Thr Leu Leu Gly Pro Pro Asp Ser Val
            100                 105                 110

Val Asp Val Gly Ser Thr Glu Val Thr Glu Glu Ile Phe Phe Trp Ser
        115                 120                 125

Thr Ser Pro Pro Trp Gly Ser Pro Cys Phe Arg Gly Glu Ala Tyr Asn
130                 135                 140

Leu Phe Glu His Asn Cys Asn Thr Phe Ser Asn Glu Val Ala Gln Phe
145                 150                 155                 160

Leu Thr Gly Arg Lys Ile Pro Ser Tyr Ile Thr Asp Leu Pro Ser Glu
                165                 170                 175

Val Leu Ser Thr Pro Phe Gly Gln Ala Leu Arg Pro Leu Leu Asp Ser
            180                 185                 190

Ile Gln Ile Gln Pro Pro Gly Gly Ser Ser Val Gly Arg Pro Asn Gly
        195                 200                 205

Gln Ser
    210
```

<210> SEQ ID NO 7
<211> LENGTH: 1318
<212> TYPE: DNA
<213> ORGANISM: Homo sapiens
<220> FEATURE:
<221> NAME/KEY: CDS
<222> LOCATION: (177)..(1190)

<400> SEQUENCE: 7

```
cgggaaggat tgaatacgag acgctgtctg cttgctgcct taagacagct agctgaattg      60
ctgattaact tttaaaatac ccagcttggt ttatttttct tagaatctgt tgctaagact     120
ggggacgctg ttttcttta caaagggaaa tctaagttaa tttcaaggca ttcgaa atg      179
                                                                Met
                                                                  1 ggg aaa gac tat tat tgc att ttg gga att gag aaa gga gct tca gat       227
Gly Lys Asp Tyr Tyr Cys Ile Leu Gly Ile Glu Lys Gly Ala Ser Asp
        5                   10                  15 gaa gat att aaa aag gct tac cga aaa caa gcc ctc aaa ttt cat ccg       275
```

-continued

| | | | | | | | | | | | | |
|---|---|---|---|---|---|---|---|---|---|---|---|---|
| Glu | Asp | Ile | Lys | Lys | Ala | Tyr | Arg | Lys | Gln | Ala | Leu | Lys | Phe | His | Pro |
| | | | 20 | | | | 25 | | | | 30 | | | | |

```
gac aag aac aaa tct cct cag gca gag gaa aaa ttt aaa gag gtc gca      323
Asp Lys Asn Lys Ser Pro Gln Ala Glu Glu Lys Phe Lys Glu Val Ala
         35                  40                  45 gaa gct tat gaa gta ttg agt gat cct aaa aag aga gaa ata tat gat      371
Glu Ala Tyr Glu Val Leu Ser Asp Pro Lys Lys Arg Glu Ile Tyr Asp
 50                  55                  60                  65 cag ttt ggg gag gaa ggg ttg aaa gga gga gca gga ggt act gat gga      419
Gln Phe Gly Glu Glu Gly Leu Lys Gly Gly Ala Gly Gly Thr Asp Gly
                     70                  75                  80 caa gga ggt acc ttc cgg tac acc ttt cat ggc gat cct cat gct aca      467
Gln Gly Gly Thr Phe Arg Tyr Thr Phe His Gly Asp Pro His Ala Thr
             85                  90                  95 ttt gct gca ttt ttc gga ggg tcc aac ccc ttt gaa att ttc ttt gga      515
Phe Ala Ala Phe Phe Gly Gly Ser Asn Pro Phe Glu Ile Phe Phe Gly
                100                 105                 110 aga cga atg ggt ggt ggt aga gat tct gaa gaa atg gaa ata gat ggt      563
Arg Arg Met Gly Gly Gly Arg Asp Ser Glu Glu Met Glu Ile Asp Gly
        115                 120                 125 gat cct ttt agt gcc ttt ggt ttc agc atg aat gga tat cca aga gac      611
Asp Pro Phe Ser Ala Phe Gly Phe Ser Met Asn Gly Tyr Pro Arg Asp
130                 135                 140                 145 agg aat tct gtg ggg cca tcc cgc ctc aaa caa gat cct cca gtt att      659
Arg Asn Ser Val Gly Pro Ser Arg Leu Lys Gln Asp Pro Pro Val Ile
                    150                 155                 160 cat gaa ctt aga gta tca ctt gaa gag ata tat agt ggt tgt acc aaa      707
His Glu Leu Arg Val Ser Leu Glu Glu Ile Tyr Ser Gly Cys Thr Lys
                165                 170                 175 cgg atg aag att tct cga aaa agg cta aac gct gat gga agg agt tac      755
Arg Met Lys Ile Ser Arg Lys Arg Leu Asn Ala Asp Gly Arg Ser Tyr
            180                 185                 190 aga tct gag gac aaa att ctt acc att gag att aaa aaa ggg tgg aaa      803
Arg Ser Glu Asp Lys Ile Leu Thr Ile Glu Ile Lys Lys Gly Trp Lys
Arg Ser
195                 200                 205 gaa ggc acc aaa att act ttt cca aga gaa gga gat gaa aca cca aat      851
Glu Gly Thr Lys Ile Thr Phe Pro Arg Glu Gly Asp Glu Thr Pro Asn
210                 215                 220                 225 agt att cca gca gac att gtt ttt atc att aaa gac aaa gat cat cca      899
Ser Ile Pro Ala Asp Ile Val Phe Ile Ile Lys Asp Lys Asp His Pro
                230                 235                 240 aaa ttt aaa agg gat gga tca aat ata att tat act gct aaa att agt      947
Lys Phe Lys Arg Asp Gly Ser Asn Ile Ile Tyr Thr Ala Lys Ile Ser
                    245                 250                 255 tta cga gag gca ttg tgt ggc tgc tca att aat gta cca aca ctg gat      995
Leu Arg Glu Ala Leu Cys Gly Cys Ser Ile Asn Val Pro Thr Leu Asp
                260                 265                 270 gga aga aac ata cct atg tca gta aat gat att gtg aaa ccc gga atg     1043
Gly Arg Asn Ile Pro Met Ser Val Asn Asp Ile Val Lys Pro Gly Met
            275                 280                 285 agg aga aga att att gga tat ggg ctg cca ttt cca aaa aat cct gac     1091
Arg Arg Arg Ile Ile Gly Tyr Gly Leu Pro Phe Pro Lys Asn Pro Asp
290                 295                 300                 305 caa cgt ggt gac ctt cta ata gaa ttt gag gtg tcc ttc cca gat act     1139
Gln Arg Gly Asp Leu Leu Ile Glu Phe Glu Val Ser Phe Pro Asp Thr
                310                 315                 320 ata tct tct tca tcc aaa gaa gta ctt agg aaa cat ctt cct gcc tca     1187
Ile Ser Ser Ser Ser Lys Glu Val Leu Arg Lys His Leu Pro Ala Ser
                    325                 330                 335
```

-continued

```
tag aatgaagaac tttgttacac atattttgat aaggcactga aaatataaaa        1240
ggactggtag tttactgatg tagatgtgaa ttctgtataa agatgtgtaa attgttttga  1300
gggttcatta aattgcat                                                1318
```

<210> SEQ ID NO 8
<211> LENGTH: 337
<212> TYPE: PRT
<213> ORGANISM: Homo sapiens

<400> SEQUENCE: 8

```
Met Gly Lys Asp Tyr Tyr Cys Ile Leu Gly Ile Glu Lys Gly Ala Ser
1               5                   10                  15

Asp Glu Asp Ile Lys Lys Ala Tyr Arg Lys Gln Ala Leu Lys Phe His
            20                  25                  30

Pro Asp Lys Asn Lys Ser Pro Gln Ala Glu Glu Lys Phe Lys Glu Val
        35                  40                  45

Ala Glu Ala Tyr Glu Val Leu Ser Asp Pro Lys Lys Arg Glu Ile Tyr
    50                  55                  60

Asp Gln Phe Gly Glu Glu Gly Leu Lys Gly Gly Ala Gly Gly Thr Asp
65                  70                  75                  80

Gly Gln Gly Gly Thr Phe Arg Tyr Thr Phe His Gly Asp Pro His Ala
                85                  90                  95

Thr Phe Ala Ala Phe Phe Gly Gly Ser Asn Pro Phe Glu Ile Phe Phe
            100                 105                 110

Gly Arg Arg Met Gly Gly Gly Arg Asp Ser Glu Glu Met Glu Ile Asp
        115                 120                 125

Gly Asp Pro Phe Ser Ala Phe Gly Phe Ser Met Asn Gly Tyr Pro Arg
    130                 135                 140

Asp Arg Asn Ser Val Gly Pro Ser Arg Leu Lys Gln Asp Pro Pro Val
145                 150                 155                 160

Ile His Glu Leu Arg Val Ser Leu Glu Glu Ile Tyr Ser Gly Cys Thr
                165                 170                 175

Lys Arg Met Lys Ile Ser Arg Lys Arg Leu Asn Ala Asp Gly Arg Ser
            180                 185                 190

Tyr Arg Ser Glu Asp Lys Ile Leu Thr Ile Glu Ile Lys Lys Gly Trp
        195                 200                 205

Lys Glu Gly Thr Lys Ile Thr Phe Pro Arg Glu Gly Asp Glu Thr Pro
    210                 215                 220

Asn Ser Ile Pro Ala Asp Ile Val Phe Ile Ile Lys Asp Lys Asp His
225                 230                 235                 240

Pro Lys Phe Lys Arg Asp Gly Ser Asn Ile Ile Tyr Thr Ala Lys Ile
                245                 250                 255

Ser Leu Arg Glu Ala Leu Cys Gly Cys Ser Ile Asn Val Pro Thr Leu
            260                 265                 270

Asp Gly Arg Asn Ile Pro Met Ser Val Asn Asp Ile Val Lys Pro Gly
        275                 280                 285

Met Arg Arg Arg Ile Ile Gly Tyr Gly Leu Pro Phe Pro Lys Asn Pro
    290                 295                 300

Asp Gln Arg Gly Asp Leu Leu Ile Glu Phe Glu Val Ser Phe Pro Asp
305                 310                 315                 320

Thr Ile Ser Ser Ser Lys Glu Val Leu Arg Lys His Leu Pro Ala
                325                 330                 335

Ser
```

```
<210> SEQ ID NO 9
<211> LENGTH: 532
<212> TYPE: DNA
<213> ORGANISM: Homo sapiens
<220> FEATURE:
<221> NAME/KEY: CDS
<222> LOCATION: (26)..(496)

<400> SEQUENCE: 9
gccatctgcg gtggagccgc acaaa atg cag att ttc gtg aaa acc ctt acg       52
                            Met Gln Ile Phe Val Lys Thr Leu Thr
                            1               5 ggg aag acc atc acc ctc gag gtt gaa ccc tcg gat acg ata gaa aat      100
Gly Lys Thr Ile Thr Leu Glu Val Glu Pro Ser Asp Thr Ile Glu Asn
 10              15                  20                  25 gta aag gcc aag atc cag gat aag gaa gga att cct cct gat cag cag      148
Val Lys Ala Lys Ile Gln Asp Lys Glu Gly Ile Pro Pro Asp Gln Gln
                 30                  35                  40 aga ctg atc ttt gct ggc aag cag ctg gaa gat gga cgt act ttg tct      196
Arg Leu Ile Phe Ala Gly Lys Gln Leu Glu Asp Gly Arg Thr Leu Ser
             45                  50                  55 gac tac aat att caa aag gag tct act ctt cat ctt gtg ttg aga ctt      244
Asp Tyr Asn Ile Gln Lys Glu Ser Thr Leu His Leu Val Leu Arg Leu
         60                  65                  70 cgt ggt ggt gct aag aaa agg aag aag aag tct tac acc act ccc aag      292
Arg Gly Gly Ala Lys Lys Arg Lys Lys Lys Ser Tyr Thr Thr Pro Lys
 75                  80                  85 aag aat aag cac aag aga aag aag gtt aag ctg gct gtc ctg aaa tat      340
Lys Asn Lys His Lys Arg Lys Lys Val Lys Leu Ala Val Leu Lys Tyr
 90                  95                 100                 105 tat aag gtg gat gag aat ggc aaa att agt cgc ctt cgt cga gag tgc      388
Tyr Lys Val Asp Glu Asn Gly Lys Ile Ser Arg Leu Arg Arg Glu Cys
                110                 115                 120 cct tct gat gaa tgt ggt gct ggg gtg ttt atg gca agt cac ttt gac      436
Pro Ser Asp Glu Cys Gly Ala Gly Val Phe Met Ala Ser His Phe Asp
            125                 130                 135 aga cat tat tgt ggc aaa tgt tgt ctg act tac tgt ttc aac aaa cca      484
Arg His Tyr Cys Gly Lys Cys Cys Leu Thr Tyr Cys Phe Asn Lys Pro
        140                 145                 150 gaa gac aag taa ctgtatgagt taataaaaga catgaactaa caaaaa              532
Glu Asp Lys
    155

<210> SEQ ID NO 10
<211> LENGTH: 156
<212> TYPE: PRT
<213> ORGANISM: Homo sapiens

<400> SEQUENCE: 10

Met Gln Ile Phe Val Lys Thr Leu Thr Gly Lys Thr Ile Thr Leu Glu
1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Ser Tyr Thr Thr Pro Lys Lys Asn Lys His Lys Arg Lys
```

-continued

```
                            85                  90                      95
Lys Val Lys Leu Ala Val Leu Lys Tyr Tyr Lys Val Asp Glu Asn Gly
                100                 105                 110

Lys Ile Ser Arg Leu Arg Arg Glu Cys Pro Ser Asp Glu Cys Gly Ala
            115                 120                 125

Gly Val Phe Met Ala Ser His Phe Asp Arg His Tyr Cys Gly Lys Cys
        130                 135                 140

Cys Leu Thr Tyr Cys Phe Asn Lys Pro Glu Asp Lys
145                 150                 155

<210> SEQ ID NO 11
<211> LENGTH: 2608
<212> TYPE: DNA
<213> ORGANISM: Homo sapiens
<220> FEATURE:
<221> NAME/KEY: CDS
<222> LOCATION: (180)..(2591)

<400> SEQUENCE: 11
agctcgccgg cctttggtct ccaggacttg tcccagcagc ccctcgaact gagaattaca      60
ccatcggacc cctggctctg aggccttcag acttggactg tgtcacactg ccaggcttcc    120
agggctccaa cttgcagacg gcctgttgtg ggacagtctc tgtaatcgcg aaagcaacc     179 atg gaa gac ctg ggg gaa aac acc atg gtt tta tcc acc ctg aga tct      227
Met Glu Asp Leu Gly Glu Asn Thr Met Val Leu Ser Thr Leu Arg Ser
1               5                   10                  15 ttg aac aac ttc atc tct cag cgt gtg gag gga ggc tct gga ctg gat      275
Leu Asn Asn Phe Ile Ser Gln Arg Val Glu Gly Gly Ser Gly Leu Asp
                20                  25                  30 att tct acc tcg gcc cca ggt tct ctg cag atg cag tac cag cag agc      323
Ile Ser Thr Ser Ala Pro Gly Ser Leu Gln Met Gln Tyr Gln Gln Ser
            35                  40                  45 atg cag ctg gag gaa aga gca gag cag atc cgt tcg aag tcc cac ctc      371
Met Gln Leu Glu Glu Arg Ala Glu Gln Ile Arg Ser Lys Ser His Leu
        50                  55                  60 atc cag gtg gag cgg gag aaa atg cag atg gag ctg agt cac aag agg      419
Ile Gln Val Glu Arg Glu Lys Met Gln Met Glu Leu Ser His Lys Arg
65                  70                  75                  80 gct cga gtg gag ctg gag aga gca gcc agc acc agt gcc agg aac tac      467
Ala Arg Val Glu Leu Glu Arg Ala Ala Ser Thr Ser Ala Arg Asn Tyr
                85                  90                  95 gag cgt gag gtc gac cgc aac cag gag ctc ctg acg cgc atc cgg cag      515
Glu Arg Glu Val Asp Arg Asn Gln Glu Leu Leu Thr Arg Ile Arg Gln
                100                 105                 110 ctt cag gag cgg gag gcc ggg gcg gag gag aag atg cag gag cag ctg      563
Leu Gln Glu Arg Glu Ala Gly Ala Glu Glu Lys Met Gln Glu Gln Leu
            115                 120                 125 gag cgc aac agg cag tgt cag cag aac ttg gat gct gcc agc aag agg      611
Glu Arg Asn Arg Gln Cys Gln Gln Asn Leu Asp Ala Ala Ser Lys Arg
        130                 135                 140 ctg cgt gag aaa gag gac agt ctg gcc cag gct ggc gag acc atc aac      659
Leu Arg Glu Lys Glu Asp Ser Leu Ala Gln Ala Gly Glu Thr Ile Asn
145                 150                 155                 160 gca ctg aag ggg agg atc tcg gaa ctg cag tgg agc gtg atg gac cag      707
Ala Leu Lys Gly Arg Ile Ser Glu Leu Gln Trp Ser Val Met Asp Gln
                165                 170                 175 gag atg cgg gtg aag cgc ctg gag tcg gag aag cag gac gtg cag gag      755
Glu Met Arg Val Lys Arg Leu Glu Ser Glu Lys Gln Asp Val Gln Glu
                180                 185                 190
```

```
cag ctg gac ctg caa cac aaa aaa tgc cag gaa gcc aat cag aaa atc      803
Gln Leu Asp Leu Gln His Lys Lys Cys Gln Glu Ala Asn Gln Lys Ile
        195                 200                 205 cag gaa ctc cag gcc agc caa gaa gca aga gca gac cac gag cag cag      851
Gln Glu Leu Gln Ala Ser Gln Glu Ala Arg Ala Asp His Glu Gln Gln
    210                 215                 220 att aag gat ctg gag cag aag ctg tcc ctg caa gag cag gat gca gcg      899
Ile Lys Asp Leu Glu Gln Lys Leu Ser Leu Gln Glu Gln Asp Ala Ala
225                 230                 235                 240 att gtg aag aac atg aag tct gag ctg gta cgg ctc cct agg ctg gaa      947
Ile Val Lys Asn Met Lys Ser Glu Leu Val Arg Leu Pro Arg Leu Glu
            245                 250                 255 cgg gag ctg gag cag ctg cgg gag gag agc gca ctg cgg gag atg aga      995
Arg Glu Leu Glu Gln Leu Arg Glu Glu Ser Ala Leu Arg Glu Met Arg
        260                 265                 270 gag acc aac ggg ctg ctc cag gaa gag ctg gaa ggg ctg cag agg aag     1043
Glu Thr Asn Gly Leu Leu Gln Glu Glu Leu Glu Gly Leu Gln Arg Lys
    275                 280                 285 ctg ggg cgc cag gag aag atg cag gag acg ctg gtt ggc ttg gag ctg     1091
Leu Gly Arg Gln Glu Lys Met Gln Glu Thr Leu Val Gly Leu Glu Leu
290                 295                 300 gag aac gag agg ctg ctg gcc aag ctg caa agc tgg gag aga ctg gac     1139
Glu Asn Glu Arg Leu Leu Ala Lys Leu Gln Ser Trp Glu Arg Leu Asp
305                 310                 315                 320 cag acc atg ggc ctg agc atc agg act cca gaa gac ctt tcc aga ttc     1187
Gln Thr Met Gly Leu Ser Ile Arg Thr Pro Glu Asp Leu Ser Arg Phe
                325                 330                 335 gtg gtt gag ctg cag cag agg gag ctt gcc ttg aag gac aag aac agc     1235
Val Val Glu Leu Gln Gln Arg Glu Leu Ala Leu Lys Asp Lys Asn Ser
            340                 345                 350 gcc gtc acc agc agc gcc cgg ggg ctg gag aag gcc agg cag cag ctg     1283
Ala Val Thr Ser Ser Ala Arg Gly Leu Glu Lys Ala Arg Gln Gln Leu
        355                 360                 365 cag gag gag ctc cgg cag gtc agc ggc cag ctg ttg gag gag agg aag     1331
Gln Glu Glu Leu Arg Gln Val Ser Gly Gln Leu Leu Glu Glu Arg Lys
    370                 375                 380 aag cgc gag acc cac gag gcg ctg gcc cgg agg ctc cag aaa cgg gtc     1379
Lys Arg Glu Thr His Glu Ala Leu Ala Arg Arg Leu Gln Lys Arg Val
385                 390                 395                 400 ctg ctc ctc acc aag gag cgg gac ggt atg cgg gcc atc ctg ggg tcc     1427
Leu Leu Leu Thr Lys Glu Arg Asp Gly Met Arg Ala Ile Leu Gly Ser
                405                 410                 415 tac gac agc gag ctg acc ccg gcc gag tac tca ccc cag ctg acg cgg     1475
Tyr Asp Ser Glu Leu Thr Pro Ala Glu Tyr Ser Pro Gln Leu Thr Arg
            420                 425                 430 cgc atg cgg gag gct gag gat atg gtg cag aag gtg cac agc cac agc     1523
Arg Met Arg Glu Ala Glu Asp Met Val Gln Lys Val His Ser His Ser
        435                 440                 445 gcc gag atg gag gct cag ctg tcg cag gcc ctg gag gag ctg gga ggc     1571
Ala Glu Met Glu Ala Gln Leu Ser Gln Ala Leu Glu Glu Leu Gly Gly
    450                 455                 460 cag aaa caa aga gca gac atg ctg gag atg gag ctg aag atg ctg aag     1619
Gln Lys Gln Arg Ala Asp Met Leu Glu Met Glu Leu Lys Met Leu Lys
465                 470                 475                 480 tct cag tcc agc tct gcc gaa cag agc ttc ctg ttc tcc agg gag gag     1667
Ser Gln Ser Ser Ser Ala Glu Gln Ser Phe Leu Phe Ser Arg Glu Glu
                485                 490                 495 gcg gac acg ctc agg ttg aag gtc gag gag ctg gaa ggc gag cgg agt     1715
Ala Asp Thr Leu Arg Leu Lys Val Glu Glu Leu Glu Gly Glu Arg Ser
            500                 505                 510
```

```
cgg ctg gag gag gaa aag agg atg ctg gag gca cag ctg gag cgg cga    1763
Arg Leu Glu Glu Lys Arg Met Leu Glu Ala Gln Leu Glu Arg Arg
        515                 520                 525 gct ctg cag ggt gac tat gac cag agc agg acc aaa gtg ctg cac atg    1811
Ala Leu Gln Gly Asp Tyr Asp Gln Ser Arg Thr Lys Val Leu His Met
530                 535                 540 agc ctg aac ccc acc agt gtg gcc agg cag cgc ctg cgc gag gac cac    1859
Ser Leu Asn Pro Thr Ser Val Ala Arg Gln Arg Leu Arg Glu Asp His
545                 550                 555                 560 agc cag ctg cag gcg gag tgc gag cga ctg cgc ggg ctc ctg cgc gcc    1907
Ser Gln Leu Gln Ala Glu Cys Glu Arg Leu Arg Gly Leu Leu Arg Ala
                565                 570                 575 atg gag aga gga ggc acc gtc cca gcc gac ctt gag gct gcc gcc gcg    1955
Met Glu Arg Gly Gly Thr Val Pro Ala Asp Leu Glu Ala Ala Ala Ala
            580                 585                 590 agt ctg cca tcg tcc aag gag gtg gca gag ctg aag aag cag gtg gag    2003
Ser Leu Pro Ser Ser Lys Glu Val Ala Glu Leu Lys Lys Gln Val Glu
        595                 600                 605 agt gcc gag ctg aag aac cag cgg ctc aag gag gtt ttc cag acc aag    2051
Ser Ala Glu Leu Lys Asn Gln Arg Leu Lys Glu Val Phe Gln Thr Lys
    610                 615                 620 atc cag gag ttc cgc aag gcc tgc tac acg ctc acc ggc tac cag atc    2099
Ile Gln Glu Phe Arg Lys Ala Cys Tyr Thr Leu Thr Gly Tyr Gln Ile
625                 630                 635                 640 gac atc acc acg gag aac cag tac cgg ctg acc tcg ctg tac gcc gag    2147
Asp Ile Thr Thr Glu Asn Gln Tyr Arg Leu Thr Ser Leu Tyr Ala Glu
                645                 650                 655 cac cca ggc gac tgc tca tct tca agg cca cca gcc cct cgg gtt cca    2195
His Pro Gly Asp Cys Ser Ser Ser Arg Pro Pro Ala Pro Arg Val Pro
            660                 665                 670 aga tgc agc tac tgg aga cag agt tct cac aca ccg tgg gcg agc tca    2243
Arg Cys Ser Tyr Trp Arg Gln Ser Ser His Thr Pro Trp Ala Ser Ser
        675                 680                 685 tcg agg tgc acc tgc ggc gcc agg aca gca tcc ctg cct tcc tca gct    2291
Ser Arg Cys Thr Cys Gly Ala Arg Thr Ala Ser Leu Pro Ser Ser Ala
    690                 695                 700 cgc tca ccc tcg agc tct tca gcc gcc aga ccg tgg cgt agc ctg cag    2339
Arg Ser Pro Ser Ser Ser Ala Ala Arg Pro Trp Arg Ser Leu Gln
705                 710                 715                 720 gct cgg ggg cat agc cgg agc cac tct gct tgg cct gac ctg cag gtc    2387
Ala Arg Gly His Ser Arg Ser His Ser Ala Trp Pro Asp Leu Gln Val
                725                 730                 735 ccc tgc ccc gcc agc cac agg ctg ggt gca cgt cct gcc tct cca gcc    2435
Pro Cys Pro Ala Ser His Arg Leu Gly Ala Arg Pro Ala Ser Pro Ala
            740                 745                 750 cca cag ggc agc agc atg act gac aga cac gct ggg acc tac gtc ggg    2483
Pro Gln Gly Ser Ser Met Thr Asp Arg His Ala Gly Thr Tyr Val Gly
        755                 760                 765 ctt cct gct ggg gcg gcc agc acc ctc tcc acg tgc aga ccc cat gcg    2531
Leu Pro Ala Gly Ala Ala Ser Thr Leu Ser Thr Cys Arg Pro His Ala
    770                 775                 780 tcc cgg agc ctg gtg tgt ggg cgt cgg cca cca gcc tgg gtt cct cac    2579
Ser Arg Ser Leu Val Cys Gly Arg Arg Pro Pro Ala Trp Val Pro His
785                 790                 795                 800 ctt gtg aaa taa aatcttctcc cctaaaa                                 2608
Leu Val Lys

<210> SEQ ID NO 12
<211> LENGTH: 803
```

```
<212> TYPE: PRT
<213> ORGANISM: Homo sapiens

<400> SEQUENCE: 12

Met Glu Asp Leu Gly Glu Asn Thr Met Val Leu Ser Thr Leu Arg Ser
 1               5                  10                  15

Leu Asn Asn Phe Ile Ser Gln Arg Val Glu Gly Gly Ser Gly Leu Asp
                20                  25                  30

Ile Ser Thr Ser Ala Pro Gly Ser Leu Gln Met Gln Tyr Gln Gln Ser
                35                  40                  45

Met Gln Leu Glu Glu Arg Ala Glu Gln Ile Arg Ser Lys Ser His Leu
 50                  55                  60

Ile Gln Val Glu Arg Glu Lys Met Gln Met Glu Leu Ser His Lys Arg
65                  70                  75                  80

Ala Arg Val Glu Leu Glu Arg Ala Ala Ser Thr Ser Ala Arg Asn Tyr
                85                  90                  95

Glu Arg Glu Val Asp Arg Asn Gln Glu Leu Leu Thr Arg Ile Arg Gln
                100                 105                 110

Leu Gln Glu Arg Glu Ala Gly Ala Glu Glu Lys Met Gln Glu Gln Leu
                115                 120                 125

Glu Arg Asn Arg Gln Cys Gln Gln Asn Leu Asp Ala Ala Ser Lys Arg
130                 135                 140

Leu Arg Glu Lys Glu Asp Ser Leu Ala Gln Ala Gly Glu Thr Ile Asn
145                 150                 155                 160

Ala Leu Lys Gly Arg Ile Ser Glu Leu Gln Trp Ser Val Met Asp Gln
                165                 170                 175

Glu Met Arg Val Lys Arg Leu Glu Ser Glu Lys Gln Asp Val Gln Glu
                180                 185                 190

Gln Leu Asp Leu Gln His Lys Lys Cys Gln Glu Ala Asn Gln Lys Ile
                195                 200                 205

Gln Glu Leu Gln Ala Ser Gln Glu Ala Arg Ala Asp His Glu Gln Gln
                210                 215                 220

Ile Lys Asp Leu Glu Gln Lys Leu Ser Leu Gln Glu Gln Asp Ala Ala
225                 230                 235                 240

Ile Val Lys Asn Met Lys Ser Glu Leu Val Arg Leu Pro Arg Leu Glu
                245                 250                 255

Arg Glu Leu Glu Gln Leu Arg Glu Ser Ala Leu Arg Glu Met Arg
                260                 265                 270

Glu Thr Asn Gly Leu Leu Gln Glu Glu Leu Glu Gly Leu Gln Arg Lys
                275                 280                 285

Leu Gly Arg Gln Glu Lys Met Gln Glu Thr Leu Val Gly Leu Glu Leu
                290                 295                 300

Glu Asn Glu Arg Leu Leu Ala Lys Leu Gln Ser Trp Glu Arg Leu Asp
305                 310                 315                 320

Gln Thr Met Gly Leu Ser Ile Arg Thr Pro Glu Asp Leu Ser Arg Phe
                325                 330                 335

Val Val Glu Leu Gln Gln Arg Gly Leu Ala Leu Lys Asp Lys Asn Ser
                340                 345                 350

Ala Val Thr Ser Ser Ala Arg Gly Leu Glu Lys Ala Arg Gln Gln Leu
                355                 360                 365

Gln Glu Glu Leu Arg Gln Val Ser Gly Gln Leu Leu Glu Glu Arg Lys
                370                 375                 380

Lys Arg Glu Thr His Glu Ala Leu Ala Arg Arg Leu Gln Lys Arg Val
385                 390                 395                 400
```

-continued

```
Leu Leu Leu Thr Lys Glu Arg Asp Gly Met Arg Ala Ile Leu Gly Ser
            405                 410                 415
Tyr Asp Ser Glu Leu Thr Pro Ala Glu Tyr Ser Pro Gln Leu Thr Arg
        420                 425                 430
Arg Met Arg Glu Ala Glu Asp Met Val Gln Lys Val His Ser His Ser
        435                 440                 445
Ala Glu Met Glu Ala Gln Leu Ser Gln Ala Leu Glu Glu Leu Gly Gly
    450                 455                 460
Gln Lys Gln Arg Ala Asp Met Leu Glu Met Glu Leu Lys Met Leu Lys
465                 470                 475                 480
Ser Gln Ser Ser Ser Ala Glu Gln Ser Phe Leu Phe Ser Arg Glu Glu
                485                 490                 495
Ala Asp Thr Leu Arg Leu Lys Val Glu Glu Leu Glu Gly Glu Arg Ser
            500                 505                 510
Arg Leu Glu Glu Glu Lys Arg Met Leu Glu Ala Gln Leu Glu Arg Arg
        515                 520                 525
Ala Leu Gln Gly Asp Tyr Asp Gln Ser Arg Thr Lys Val Leu His Met
    530                 535                 540
Ser Leu Asn Pro Thr Ser Val Ala Arg Gln Arg Leu Arg Glu Asp His
545                 550                 555                 560
Ser Gln Leu Gln Ala Glu Cys Glu Arg Leu Arg Gly Leu Leu Arg Ala
                565                 570                 575
Met Glu Arg Gly Gly Thr Val Pro Ala Asp Leu Glu Ala Ala Ala Ala
            580                 585                 590
Ser Leu Pro Ser Ser Lys Glu Val Ala Glu Leu Lys Lys Gln Val Glu
        595                 600                 605
Ser Ala Glu Leu Lys Asn Gln Arg Leu Lys Glu Val Phe Gln Thr Lys
    610                 615                 620
Ile Gln Glu Phe Arg Lys Ala Cys Tyr Thr Leu Thr Gly Tyr Gln Ile
625                 630                 635                 640
Asp Ile Thr Thr Glu Asn Gln Tyr Arg Leu Thr Ser Leu Tyr Ala Glu
                645                 650                 655
His Pro Gly Asp Cys Ser Ser Arg Pro Ala Pro Arg Val Pro
            660                 665                 670                 Pro
Arg Cys Ser Tyr Trp Arg Gln Ser His Thr Pro Trp Ala Ser Ser
        675                 680                 685
Ser Arg Cys Thr Cys Gly Ala Arg Thr Ala Ser Leu Pro Ser Ser Ala
    690                 695                 700
Arg Ser Pro Ser Ser Ser Ala Ala Arg Pro Trp Arg Ser Leu Gln
705                 710                 715                 720
Ala Arg Gly His Ser Arg Ser His Ser Ala Trp Pro Asp Leu Gln Val
                725                 730                 735
Pro Cys Pro Ala Ser His Arg Leu Gly Ala Arg Pro Ala Ser Pro Ala
            740                 745                 750
Pro Gln Gly Ser Ser Met Thr Asp Arg His Ala Gly Thr Tyr Val Gly
        755                 760                 765
Leu Pro Ala Gly Ala Ala Ser Thr Leu Ser Thr Cys Arg Pro His Ala
    770                 775                 780
Ser Arg Ser Leu Val Cys Gly Arg Arg Pro Pro Ala Trp Val Pro His
785                 790                 795                 800
Leu Val Lys
```

-continued

```
<210> SEQ ID NO 13
<211> LENGTH: 2965
<212> TYPE: DNA
<213> ORGANISM: Homo sapiens
<220> FEATURE:
<221> NAME/KEY: CDS
<222> LOCATION: (189)..(2777)

<400> SEQUENCE: 13
gcggaggtcg gcggtcgggt ccgtctctgc ccgcggctgt ggcggcgccg gcggatccag      60
ccttagcgtt cctctctggg cggcggcggc ggcggctcgg ttgacgcctc ctccgccagc     120
tgagcccgcg ggagcccagg acgccgcttc cccgcccatc cccgctcccc gaggccggcc     180 gcctggtc atg gcg cag ccg ggc ccg gct tcc cag cct gac gtt tct ctt     230
         Met Ala Gln Pro Gly Pro Ala Ser Gln Pro Asp Val Ser Leu
           1               5                  10 cag caa cgg gta gca gaa ttg gaa aaa att aat gca gaa ttt tta cgt      278
Gln Gln Arg Val Ala Glu Leu Glu Lys Ile Asn Ala Glu Phe Leu Arg
 15              20                  25                  30 gca caa cag cag ctt gaa caa gaa ttt aat caa aag aga gca aaa ttt      326
Ala Gln Gln Gln Leu Glu Gln Glu Phe Asn Gln Lys Arg Ala Lys Phe
                 35                  40                  45 aag gag tta tat ttg gct aaa gag gag gat ctg aag agg caa aat gca      374
Lys Glu Leu Tyr Leu Ala Lys Glu Glu Asp Leu Lys Arg Gln Asn Ala
             50                  55                  60 gta tta caa gct gca caa gat gat ttg gga cac ctt cga acc cag ctg      422
Val Leu Gln Ala Ala Gln Asp Asp Leu Gly His Leu Arg Thr Gln Leu
 65                  70                  75 tgg gaa gct caa gca gag atg gag aat att aag gcg att gcc aca gtc      470
Trp Glu Ala Gln Ala Glu Met Glu Asn Ile Lys Ala Ile Ala Thr Val
 80                  85                  90 tct gag aac acc aag caa gaa gct ata gat gaa gtg aaa aga cag tgg      518
Ser Glu Asn Thr Lys Gln Glu Ala Ile Asp Glu Val Lys Arg Gln Trp
 95                 100                 105                 110 aga gaa gaa gtt gct tca ctt cag gct gtt atg aaa gaa aca gtt cgt      566
Arg Glu Glu Val Ala Ser Leu Gln Ala Val Met Lys Glu Thr Val Arg
                115                 120                 125 gac tat gag cac cag ttc cac ctt agg ctg gag cag gag cga aca cag      614
Asp Tyr Glu His Gln Phe His Leu Arg Leu Glu Gln Glu Arg Thr Gln
                130                 135                 140 tgg gca cag tat aga gaa tac gca gag agg gaa ata gct gat tta aga      662
Trp Ala Gln Tyr Arg Glu Tyr Ala Glu Arg Glu Ile Ala Asp Leu Arg
            145                 150                 155 aga agg ctg tct gaa ggt caa gag gag gaa aat tta gaa aat gaa atg      710
Arg Arg Leu Ser Glu Gly Gln Glu Glu Glu Asn Leu Glu Asn Glu Met
 160                 165                 170 aaa aag gcc caa gag gat gct gag aaa ctt cgg tcc gtt gtg atg cca      758
Lys Lys Ala Gln Glu Asp Ala Glu Lys Leu Arg Ser Val Val Met Pro
175                 180                 185                 190 atg gaa aag gaa att gca gct ttg aag gat aaa ctg aca gag gct gaa      806
Met Glu Lys Glu Ile Ala Ala Leu Lys Asp Lys Leu Thr Glu Ala Glu
                195                 200                 205 gac aaa att aaa gag ctg gag gcc tca aag gtt aaa gaa ctg aat cat      854
Asp Lys Ile Lys Glu Leu Glu Ala Ser Lys Val Lys Glu Leu Asn His
                210                 215                 220 tat ctg gaa gct gag aaa tct tgt agg act gat cta gag atg tat gta      902
Tyr Leu Glu Ala Glu Lys Ser Cys Arg Thr Asp Leu Glu Met Tyr Val
            225                 230                 235 gct gtt ttg aat act cag aaa tct gtt cta cag gaa gat gct gag aaa      950
Ala Val Leu Asn Thr Gln Lys Ser Val Leu Gln Glu Asp Ala Glu Lys
 240                 245                 250
```

```
ctg cgg aaa gaa ttg cat gaa gtt tgc cat ctc ttg gag caa gag cga    998
Leu Arg Lys Glu Leu His Glu Val Cys His Leu Leu Glu Gln Glu Arg
255                 260                 265                 270 caa caa cac aac cag tta aaa cat acg tgg cag aag gcc aat gac cag   1046
Gln Gln His Asn Gln Leu Lys His Thr Trp Gln Lys Ala Asn Asp Gln
                275                 280                 285 ttt ctg gaa tct cag cgt tta ctg atg aga gac atg cag cga atg gag   1094
Phe Leu Glu Ser Gln Arg Leu Leu Met Arg Asp Met Gln Arg Met Glu
            290                 295                 300 att gtg cta act tca gaa cag ctc cga caa gtt gaa gaa ctg aag aag   1142
Ile Val Leu Thr Ser Glu Gln Leu Arg Gln Val Glu Glu Leu Lys Lys
        305                 310                 315 aaa gat cag gag gat gat gaa caa caa aga ctc aat aag aga aag gat   1190
Lys Asp Gln Glu Asp Asp Glu Gln Gln Arg Leu Asn Lys Arg Lys Asp
320                 325                 330 cac aaa aaa gca gat gtt gag gaa gaa ata aaa ata cca gta gtg tgt   1238
His Lys Lys Ala Asp Val Glu Glu Glu Ile Lys Ile Pro Val Val Cys
335                 340                 345                 350 gct tta act caa gaa gaa tct tca gcc cag tta tca aat gaa gag gag   1286
Ala Leu Thr Gln Glu Glu Ser Ser Ala Gln Leu Ser Asn Glu Glu Glu
                355                 360                 365 cat tta gac agc acc cgt ggc tca gtt cat tcc tta gat gca ggc ttg   1334
His Leu Asp Ser Thr Arg Gly Ser Val His Ser Leu Asp Ala Gly Leu
            370                 375                 380 ctg ttg cca tct gga gat cct ttc agt aaa tcg gac aat gac atg ttt   1382
Leu Leu Pro Ser Gly Asp Pro Phe Ser Lys Ser Asp Asn Asp Met Phe
        385                 390                 395 aaa gat gga ctc agg aga gca cag tct aca gac agc ttg gga acc tcg   1430
Lys Asp Gly Leu Arg Arg Ala Gln Ser Thr Asp Ser Leu Gly Thr Ser
400                 405                 410 ggc tca ttg caa tcc aaa gct tta ggc tat aac tac aaa gca aaa tct   1478
Gly Ser Leu Gln Ser Lys Ala Leu Gly Tyr Asn Tyr Lys Ala Lys Ser
415                 420                 425                 430 gct gga aac ctg gac gag tca gat ttt gga cca ctg gta gga gca gat   1526
Ala Gly Asn Leu Asp Glu Ser Asp Phe Gly Pro Leu Val Gly Ala Asp
                435                 440                 445 tca gtg tct gag aac ttt gat act gca tcc ctt ggg tca ctc cag atg   1574
Ser Val Ser Glu Asn Phe Asp Thr Ala Ser Leu Gly Ser Leu Gln Met
            450                 455                 460 cca agt ggg ttt atg tta acc aaa gat cag gaa aga gca atc aag gcg   1622
Pro Ser Gly Phe Met Leu Thr Lys Asp Gln Glu Arg Ala Ile Lys Ala
        465                 470                 475 atg aca cca gaa caa gaa gag aca gcg tcc ctc ctc tcc agc gtt acc   1670
Met Thr Pro Glu Gln Glu Glu Thr Ala Ser Leu Leu Ser Ser Val Thr
480                 485                 490 cag ggc atg gag agt gcc tat gtg tcc cct agt ggt tat cgt tta gtt   1718
Gln Gly Met Glu Ser Ala Tyr Val Ser Pro Ser Gly Tyr Arg Leu Val
495                 500                 505                 510 agt gaa aca gaa tgg aat ctc ttg cag aaa gag gta cat aat gct gga   1766
Ser Glu Thr Glu Trp Asn Leu Leu Gln Lys Glu Val His Asn Ala Gly
                515                 520                 525 aat aaa ctt ggt aga cgt tgt gat atg tgt ccc aat tac gaa aaa cag   1814
Asn Lys Leu Gly Arg Arg Cys Asp Met Cys Ser Asn Tyr Glu Lys Gln
            530                 535                 540 tta caa gga att cag att cag gag gct gaa acg aga gac cag gtg aaa   1862
Leu Gln Gly Ile Gln Ile Gln Glu Ala Glu Thr Arg Asp Gln Val Lys
        545                 550                 555 aaa cta cag ctg atg cta agg caa gct aat gac cag tta gag aag aca   1910
Lys Leu Gln Leu Met Leu Arg Gln Ala Asn Asp Gln Leu Glu Lys Thr
```

```
                560                 565                 570
atg aaa gat aag cag gag ctg gaa gac ttc ata aag caa agc agc gaa    1958
Met Lys Asp Lys Gln Glu Leu Glu Asp Phe Ile Lys Gln Ser Ser Glu
575             580                 585                 590 gat tcg agt cac cag atc tct gca ctc gtc cta aga gcc cag gcc tcc    2006
Asp Ser Ser His Gln Ile Ser Ala Leu Val Leu Arg Ala Gln Ala Ser
                595                 600                 605 gag atc tta ctt gaa gag tta cag cag ggg ctt tcc cag gca aag agg    2054
Glu Ile Leu Leu Glu Glu Leu Gln Gln Gly Leu Ser Gln Ala Lys Arg
            610                 615                 620 gat gtt cag gaa cag atg gcg gtg ctg atg cag tca cgg gaa cag gtt    2102
Asp Val Gln Glu Gln Met Ala Val Leu Met Gln Ser Arg Glu Gln Val
        625                 630                 635 tca gaa gag ctg gtg agg tta cag aaa gat aat gac agt ctc cag gga    2150
Ser Glu Glu Leu Val Arg Leu Gln Lys Asp Asn Asp Ser Leu Gln Gly
    640                 645                 650 aag cac agc ctg cat gtg tca tta cag caa gca gaa gac ttc atc ctc    2198
Lys His Ser Leu His Val Ser Leu Gln Gln Ala Glu Asp Phe Ile Leu
655             660                 665                 670 cca gac act aca gag gca ctg cgg gag ttg gta tta aaa tac cgt gag    2246
Pro Asp Thr Thr Glu Ala Leu Arg Glu Leu Val Leu Lys Tyr Arg Glu
                675                 680                 685 gac atc att aat gtg cgg aca gca gca gac cac gta gaa gaa aag ctg    2294
Asp Ile Ile Asn Val Arg Thr Ala Ala Asp His Val Glu Glu Lys Leu
            690                 695                 700 aag gct gag ata ctt ttc cta aaa gag cag atc caa gca gaa cag tgt    2342
Lys Ala Glu Ile Leu Phe Leu Lys Glu Gln Ile Gln Ala Glu Gln Cys
        705                 710                 715 tta aaa gaa aat ctt gaa gaa act ctg caa cta gaa ata gaa aac tgc    2390
Leu Lys Glu Asn Leu Glu Glu Thr Leu Gln Leu Glu Ile Glu Asn Cys
    720                 725                 730 aag gag gaa ata gct tct att tct agc cta aaa gct gaa tta gaa aga    2438
Lys Glu Glu Ile Ala Ser Ile Ser Ser Leu Lys Ala Glu Leu Glu Arg
735             740                 745                 750 ata aaa gtg gaa aaa gga cag ttg gag tcc aca tta aga gag aag tct    2486
Ile Lys Val Glu Lys Gly Gln Leu Glu Ser Thr Leu Arg Glu Lys Ser
                755                 760                 765 caa cag ctt gag agt ctt cag gaa ata aag atc agt ttg gaa gag cag    2534
Gln Gln Leu Glu Ser Leu Gln Glu Ile Lys Ile Ser Leu Glu Glu Gln
            770                 775                 780 tta aag aaa gag act gct gct aag gct acc gtt gaa cag cta atg ttt    2582
Leu Lys Lys Glu Thr Ala Ala Lys Ala Thr Val Glu Gln Leu Met Phe
        785                 790                 795 gaa gag aag aac aaa gct cag aga tta cag aca gaa tta gat gtc agt    2630
Glu Glu Lys Asn Lys Ala Gln Arg Leu Gln Thr Glu Leu Asp Val Ser
    800                 805                 810 gag caa gtc cag aga gat ttt gta aag ctt tca cag acc ctt cag gtg    2678
Glu Gln Val Gln Arg Asp Phe Val Lys Leu Ser Gln Thr Leu Gln Val
815             820                 825                 830 cag tta gag cgg atc cgg caa gct gac tcc ttg gag aga atc cgg gca    2726
Gln Leu Glu Arg Ile Arg Gln Ala Asp Ser Leu Glu Arg Ile Arg Ala
                835                 840                 845 att ctg aat gat act aaa ctg aca gac att aac cag ctt cct gag aca    2774
Ile Leu Asn Asp Thr Lys Leu Thr Asp Ile Asn Gln Leu Pro Glu Thr
            850                 855                 860 tga caccctcatg gcaggattct agcctgcact ttgggttttt aactcatctt          2827
tagagcaaca gtaattatta tttaactctt aactgaagaa agagaagtca caacaaaagg   2887
aagactggag aaatgcttac ttctagaggg agaagactgt gcggcacagg aaacagcaaa   2947
```

-continued cagtggggtg atctgcag                                              2965

<210> SEQ ID NO 14
<211> LENGTH: 862
<212> TYPE: PRT
<213> ORGANISM: Homo sapiens

<400> SEQUENCE: 14

Met Ala Gln Pro Gly Pro Ala Ser Gln Pro Asp Val Ser Leu Gln Gln
1               5                   10                  15

Arg Val Ala Glu Leu Glu Lys Ile Asn Ala Glu Phe Leu Arg Ala Gln
            20                  25                  30

Gln Gln Leu Glu Gln Glu Phe Asn Gln Lys Arg Ala Lys Phe Lys Glu
        35                  40                  45

Leu Tyr Leu Ala Lys Glu Glu Asp Leu Lys Arg Gln Asn Ala Val Leu
    50                  55                  60

Gln Ala Ala Gln Asp Asp Leu Gly His Leu Arg Thr Gln Leu Trp Glu
65                  70                  75                  80

Ala Gln Ala Glu Met Glu Asn Ile Lys Ala Ile Ala Thr Val Ser Glu
                85                  90                  95

Asn Thr Lys Gln Glu Ala Ile Asp Glu Val Lys Arg Gln Trp Arg Glu
            100                 105                 110

Glu Val Ala Ser Leu Gln Ala Val Met Lys Glu Thr Val Arg Asp Tyr
        115                 120                 125

Glu His Gln Phe His Leu Arg Leu Glu Gln Glu Arg Thr Gln Trp Ala
    130                 135                 140

Gln Tyr Arg Glu Tyr Ala Glu Arg Glu Ile Ala Asp Leu Arg Arg Arg
145                 150                 155                 160

Leu Ser Glu Gly Gln Glu Glu Asn Leu Glu Asn Glu Met Lys Lys
                165                 170                 175

Ala Gln Glu Asp Ala Glu Lys Leu Arg Ser Val Val Met Pro Met Glu
            180                 185                 190

Lys Glu Ile Ala Ala Leu Lys Asp Lys Leu Thr Glu Ala Glu Asp Lys
        195                 200                 205

Ile Lys Glu Leu Glu Ala Ser Lys Val Lys Glu Leu Asn His Tyr Leu
    210                 215                 220

Glu Ala Glu Lys Ser Cys Arg Thr Asp Leu Glu Met Tyr Val Ala Val
225                 230                 235                 240

Leu Asn Thr Gln Lys Ser Val Leu Gln Glu Asp Ala Glu Lys Leu Arg
                245                 250                 255

Lys Glu Leu His Glu Val Cys His Leu Leu Glu Gln Glu Arg Gln Gln
            260                 265                 270

His Asn Gln Leu Lys His Thr Trp Gln Lys Ala Asn Asp Gln Phe Leu
        275                 280                 285

Glu Ser Gln Arg Leu Leu Met Arg Asp Met Gln Arg Met Glu Ile Val
    290                 295                 300

Leu Thr Ser Glu Gln Leu Arg Gln Val Glu Leu Lys Lys Lys Asp
305                 310                 315                 320

Gln Glu Asp Asp Glu Gln Gln Arg Leu Asn Lys Arg Lys Asp His Lys
                325                 330                 335

Lys Ala Asp Val Glu Glu Glu Ile Lys Ile Pro Val Val Cys Ala Leu
            340                 345                 350

Thr Gln Glu Glu Ser Ser Ala Gln Leu Ser Asn Glu Glu His Leu
        355                 360                 365

```
Asp Ser Thr Arg Gly Ser Val His Ser Leu Asp Ala Gly Leu Leu Leu
    370                 375                 380

Pro Ser Gly Asp Pro Phe Ser Lys Ser Asp Asn Asp Met Phe Lys Asp
385                 390                 395                 400

Gly Leu Arg Arg Ala Gln Ser Thr Asp Ser Leu Gly Thr Ser Gly Ser
                405                 410                 415

Leu Gln Ser Lys Ala Leu Gly Tyr Asn Tyr Lys Ala Lys Ser Ala Gly
            420                 425                 430

Asn Leu Asp Glu Ser Asp Phe Gly Pro Leu Val Gly Ala Asp Ser Val
        435                 440                 445

Ser Glu Asn Phe Asp Thr Ala Ser Leu Gly Ser Leu Gln Met Pro Ser
    450                 455                 460

Gly Phe Met Leu Thr Lys Asp Gln Glu Arg Ala Ile Lys Ala Met Thr
465                 470                 475                 480

Pro Glu Gln Glu Glu Thr Ala Ser Leu Leu Ser Val Thr Gln Gly
                485                 490                 495

Met Glu Ser Ala Tyr Val Ser Pro Ser Gly Tyr Arg Leu Val Ser Glu
                500                 505                 510

Thr Glu Trp Asn Leu Leu Gln Lys Glu Val His Asn Ala Gly Asn Lys
            515                 520                 525

Leu Gly Arg Arg Cys Asp Met Cys Ser Asn Tyr Glu Lys Gln Leu Gln
        530                 535                 540

Gly Ile Gln Ile Gln Glu Ala Glu Thr Arg Asp Gln Val Lys Lys Leu
545                 550                 555                 560

Gln Leu Met Leu Arg Gln Ala Asn Asp Gln Leu Glu Lys Thr Met Lys
                565                 570                 575

Asp Lys Gln Glu Leu Glu Asp Phe Ile Lys Gln Ser Ser Glu Asp Ser
            580                 585                 590

Ser His Gln Ile Ser Ala Leu Val Leu Arg Ala Gln Ala Ser Glu Ile
        595                 600                 605

Leu Leu Glu Glu Leu Gln Gln Gly Leu Ser Gln Ala Lys Arg Asp Val
    610                 615                 620

Gln Glu Gln Met Ala Val Leu Met Gln Ser Arg Glu Gln Val Ser Glu
625                 630                 635                 640

Glu Leu Val Arg Leu Gln Lys Asp Asn Asp Ser Leu Gln Gly Lys His
                645                 650                 655

Ser Leu His Val Ser Leu Gln Gln Ala Glu Asp Phe Ile Leu Pro Asp
            660                 665                 670

Thr Thr Glu Ala Leu Arg Glu Leu Val Leu Lys Tyr Arg Glu Asp Ile
        675                 680                 685

Ile Asn Val Arg Thr Ala Ala Asp His Val Glu Glu Lys Leu Lys Ala
    690                 695                 700

Glu Ile Leu Phe Leu Lys Glu Gln Ile Gln Ala Glu Gln Cys Leu Lys
705                 710                 715                 720

Glu Asn Leu Glu Glu Thr Leu Gln Leu Glu Ile Glu Asn Cys Lys Glu
                725                 730                 735

Glu Ile Ala Ser Ile Ser Ser Leu Lys Ala Glu Leu Glu Arg Ile Lys
            740                 745                 750

Val Glu Lys Gly Gln Leu Glu Ser Thr Leu Arg Glu Lys Ser Gln Gln
        755                 760                 765

Leu Glu Ser Leu Gln Glu Ile Lys Ile Ser Leu Glu Glu Gln Leu Lys
    770                 775                 780
```

| Lys | Glu | Thr | Ala | Ala | Lys | Ala | Thr | Val | Glu | Gln | Leu | Met | Phe | Glu | Glu |
|---|---|---|---|---|---|---|---|---|---|---|---|---|---|---|---|
| 785 | | | | 790 | | | | | 795 | | | | | 800 | |

| Lys | Asn | Lys | Ala | Gln | Arg | Leu | Gln | Thr | Glu | Leu | Asp | Val | Ser | Glu | Gln |
|---|---|---|---|---|---|---|---|---|---|---|---|---|---|---|---|
| | | | | 805 | | | | | 810 | | | | | 815 | |

| Val | Gln | Arg | Asp | Phe | Val | Lys | Leu | Ser | Gln | Thr | Leu | Gln | Val | Gln | Leu |
|---|---|---|---|---|---|---|---|---|---|---|---|---|---|---|---|
| | | | | 820 | | | | | 825 | | | | | 830 | |

| Glu | Arg | Ile | Arg | Gln | Ala | Asp | Ser | Leu | Glu | Arg | Ile | Arg | Ala | Ile | Leu |
|---|---|---|---|---|---|---|---|---|---|---|---|---|---|---|---|
| | | | 835 | | | | | 840 | | | | | 845 | | |

| Asn | Asp | Thr | Lys | Leu | Thr | Asp | Ile | Asn | Gln | Leu | Pro | Glu | Thr |
|---|---|---|---|---|---|---|---|---|---|---|---|---|---|
| | | 850 | | | | | 855 | | | | | 860 | |

<210> SEQ ID NO 15
<211> LENGTH: 1330
<212> TYPE: DNA
<213> ORGANISM: Homo sapiens
<220> FEATURE:
<221> NAME/KEY: CDS
<222> LOCATION: (145)..(1278)

<400> SEQUENCE: 15

```
aattcccaaa tgaccttta tttcatacag agatacaaag gcaactatgt gcagcaacaa      60
tctgatgggc agtccaaact cttgggagga agtaaattca tggtaaatgt catgatggcg     120
gtcgggaggg aggaaggtgg caag atg gtg ttg gaa agc act atg gtg tgt        171
                          Met Val Leu Glu Ser Thr Met Val Cys
                            1               5 gtg gac aac agt gag tat atg cgg aat gga gac ttc tta ccc acc agg       219
Val Asp Asn Ser Glu Tyr Met Arg Asn Gly Asp Phe Leu Pro Thr Arg
 10              15                  20                  25 ctg cag gcc cag cag gat gct gtc aac ata gtt tgt cat tca aag acc       267
Leu Gln Ala Gln Gln Asp Ala Val Asn Ile Val Cys His Ser Lys Thr
             30                  35                  40 cgc agc aac cct gag aac aac gtg ggc ctt atc aca ctg gct aat gac       315
Arg Ser Asn Pro Glu Asn Asn Val Gly Leu Ile Thr Leu Ala Asn Asp
         45                  50                  55 tgt gaa gtg ctg acc aca ctc acc cca gac act ggc cgt atc ctg tcc       363
Cys Glu Val Leu Thr Thr Leu Thr Pro Asp Thr Gly Arg Ile Leu Ser
     60                  65                  70 aag cta cat act gtc caa ccc aag ggc aag atc acc ttc tgc acg ggc       411
Lys Leu His Thr Val Gln Pro Lys Gly Lys Ile Thr Phe Cys Thr Gly
 75                  80                  85 atc cgc gtg gcc cat ctg gct ctg aag cac cga caa ggc aag aat cac       459
Ile Arg Val Ala His Leu Ala Leu Lys His Arg Gln Gly Lys Asn His
 90                  95                 100                 105 aag atg cgc atc att gcc ttt gtg gga agc cca gtg gag gac aat gag       507
Lys Met Arg Ile Ile Ala Phe Val Gly Ser Pro Val Glu Asp Asn Glu
                110                 115                 120 aag gat ctg gtg aaa ctg gct aaa cgc ctc aag aag gag aaa gta aat       555
Lys Asp Leu Val Lys Leu Ala Lys Arg Leu Lys Lys Glu Lys Val Asn
            125                 130                 135 gtt gac att atc aat ttt ggg gaa gag gag gtg aac aca gaa aag ctg       603
Val Asp Ile Ile Asn Phe Gly Glu Glu Glu Val Asn Thr Glu Lys Leu
        140                 145                 150 aca gcc ttt gta aac acg ttg aat ggc aaa gat gga acc ggt tct cat       651
Thr Ala Phe Val Asn Thr Leu Asn Gly Lys Asp Gly Thr Gly Ser His
    155                 160                 165 ctg gtg aca gtg cct cct ggg ccc agt ttg gct gat gct ctc atc agt       699
Leu Val Thr Val Pro Pro Gly Pro Ser Leu Ala Asp Ala Leu Ile Ser
170                 175                 180                 185 tct ccg att ttg gct ggt gaa ggt ggt gcc atg ctg ggt ctt ggt gcc       747
```

```
Ser Pro Ile Leu Ala Gly Glu Gly Gly Ala Met Leu Gly Leu Gly Ala
                190                 195                 200 agt gac ttt gaa ttt gga gta gat ccc agt gct gat cct gag ctg gcc      795
Ser Asp Phe Glu Phe Gly Val Asp Pro Ser Ala Asp Pro Glu Leu Ala
            205                 210                 215 ttg gcc ctt cgt gta tct atg gaa gag cag cgg cag cgg cag gag gag      843
Leu Ala Leu Arg Val Ser Met Glu Glu Gln Arg Gln Arg Gln Glu Glu
        220                 225                 230 gag gcc cgg cgg gca gct gca gct tct gct gct gag gcc ggg att gct      891
Glu Ala Arg Arg Ala Ala Ala Ala Ser Ala Ala Glu Ala Gly Ile Ala
    235                 240                 245 acg act ggg act gaa gac tca gac gat gcc ctg ctg aag atg acc atc      939
Thr Thr Gly Thr Glu Asp Ser Asp Asp Ala Leu Leu Lys Met Thr Ile
250                 255                 260                 265 agc cag caa gag ttt ggc cgc act ggg ctt cct gac cta agc agt atg      987
Ser Gln Gln Glu Phe Gly Arg Thr Gly Leu Pro Asp Leu Ser Ser Met
                270                 275                 280 act gag gaa gag cag att gct tat gcc atg cag atg tcc ctg cag gga     1035
Thr Glu Glu Glu Gln Ile Ala Tyr Ala Met Gln Met Ser Leu Gln Gly
            285                 290                 295 gca gag ttt ggc cag gcg gaa tca gca gac att gat gcc agc tca gct     1083
Ala Glu Phe Gly Gln Ala Glu Ser Ala Asp Ile Asp Ala Ser Ser Ala
        300                 305                 310 atg gac aca tcc gag cca gcc aag gag gag gat gat tac gac gtg atg     1131
Met Asp Thr Ser Glu Pro Ala Lys Glu Glu Asp Asp Tyr Asp Val Met
    315                 320                 325 cag gac ccc gag ttc ctt cag agt gtc cta gag aac ctc cca ggt gtg     1179
Gln Asp Pro Glu Phe Leu Gln Ser Val Leu Glu Asn Leu Pro Gly Val
330                 335                 340                 345 gat ccc aac aat gaa gcc att cga aat gct atg ggc tcc ctg gcc tcc     1227
Asp Pro Asn Asn Glu Ala Ile Arg Asn Ala Met Gly Ser Leu Ala Ser
                350                 355                 360 cag gcc acc aag gac ggc aag aag gac aag aag gag gaa gac aag aag     1275
Gln Ala Thr Lys Asp Gly Lys Lys Asp Lys Lys Glu Glu Asp Lys Lys
            365                 370                 375 tga gactggaggg aaagggtagc tgagtctgct tagggactgc atgggggaat tc       1330

<210> SEQ ID NO 16
<211> LENGTH: 377
<212> TYPE: PRT
<213> ORGANISM: Homo sapiens

<400> SEQUENCE: 16

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
                20                  25                  30

Val Asn Ile Val Cys His Ser Lys Thr Arg Ser Asn Pro Glu Asn Asn
            35                  40                  45

Val Gly Leu Ile Thr Leu Ala Asn Asp Cys Glu Val Leu Thr Thr Leu
        50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
```

```
                115                 120                 125
Lys Arg Leu Lys Lys Glu Lys Val Asn Val Asp Ile Ile Asn Phe Gly
    130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
    210                 215                 220

Glu Glu Gln Arg Gln Arg Gln Glu Glu Ala Arg Arg Ala Ala Ala
225                 230                 235                 240

Ala Ser Ala Ala Glu Ala Gly Ile Ala Thr Thr Gly Thr Glu Asp Ser
                245                 250                 255

Asp Asp Ala Leu Leu Lys Met Thr Ile Ser Gln Gln Glu Phe Gly Arg
            260                 265                 270

Thr Gly Leu Pro Asp Leu Ser Ser Met Thr Glu Glu Glu Gln Ile Ala
        275                 280                 285

Tyr Ala Met Gln Met Ser Leu Gln Gly Ala Glu Phe Gly Gln Ala Glu
    290                 295                 300

Ser Ala Asp Ile Asp Ala Ser Ser Ala Met Asp Thr Ser Glu Pro Ala
305                 310                 315                 320

Lys Glu Glu Asp Asp Tyr Asp Val Met Gln Asp Pro Glu Phe Leu Gln
                325                 330                 335

Ser Val Leu Glu Asn Leu Pro Gly Val Asp Pro Asn Asn Glu Ala Ile
            340                 345                 350

Arg Asn Ala Met Gly Ser Leu Ala Ser Gln Ala Thr Lys Asp Gly Lys
        355                 360                 365

Lys Asp Lys Lys Glu Glu Asp Lys Lys
    370                 375

<210> SEQ ID NO 17
<211> LENGTH: 294
<212> TYPE: DNA
<213> ORGANISM: Homo sapiens

<400> SEQUENCE: 17
gcggccgcgg gggcgccagc accttcggct ccggcggcgc tatcctggga gcccggagga      60
ccgccgcttt caccactctc ggccatggct gtggcggcgg cggcggcggt gactcaggca     120
agcaggaggg agcaggcgag caaggaggag ccagcagaca ccagagccgg caggcctgga     180
cagcgaagaa tgcagagcac gccgcctcag tagcaacggg cgcagggcca cggtagcggg     240
gtgtggggcc ccggagctcg gtgcaggctc tggcgcagcc cgggtcaggc gctc           294

<210> SEQ ID NO 18
<211> LENGTH: 494
<212> TYPE: DNA
<213> ORGANISM: Homo sapiens
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
```

```
<222> LOCATION: (214)..(214)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t

<400> SEQUENCE: 18
```

| | | | | | |
|---|---|---|---|---|---|
| aacaagctct | gcattcctgg | tgtgttgaac | atactagctc | ctactccagg | caccaaattt | 60 |
| ggcgcagtag | tactctgccc | agaagtgcca | ctggagtact | accagtagtg | ccacccacag | 120 |
| tgctggcagt | gccgctggaa | gctgatgaac | tctgggaagt | ctgtggagcc | catggattgg | 180 |
| gtagtggatc | tcnaatttcc | tgtacgggaa | ggtngactac | cttcaccaga | ggatgtattg | 240 |
| ctcaccaagg | aagcaaatgg | attaccacca | aactgctctt | gtgcagcact | cagcattggt | 300 |
| tcctgaatat | ctgtgtacat | gcgcctttaa | agcattatat | cccctggga | tgcttttcta | 360 |
| gggttgctca | aaagctcggg | tcctgggttc | ctcatcaatc | ctcctggcat | cattgctggg | 420 |
| attccctggg | caaggttcca | acgntttgg | cctcattatn | atctggatta | ttcaacatta | 480 |
| tgncctaaat | ttct | | | | | 494 |

```
<210> SEQ ID NO 19
<211> LENGTH: 2311
<212> TYPE: DNA
<213> ORGANISM: Xenopus laevis
<220> FEATURE:
<221> NAME/KEY: CDS
<222> LOCATION: (44)..(1801)

<400> SEQUENCE: 19
gccttcctat tgctcctcct cggggtgggc gggtgcagag aag atg gcg gag agc         55
                                             Met Ala Glu Ser
                                               1 ggc gct gat ggt gcg gcc tct ggt act acc ggg ccg gct ccg ggt aaa        103
Gly Ala Asp Gly Ala Ala Ser Gly Thr Thr Gly Pro Ala Pro Gly Lys
  5              10                  15                  20 ggt ctt att cgt gtc acc gtc aaa acg ccc aaa gac aag gaa gag atc        151
Gly Leu Ile Arg Val Thr Val Lys Thr Pro Lys Asp Lys Glu Glu Ile
             25                  30                  35 tcc agg cgg ttc aaa gcg aaa cgg gat cag ctg gtt ctg atc ttt gcc        199
Ser Arg Arg Phe Lys Ala Lys Arg Asp Gln Leu Val Leu Ile Phe Ala
         40                  45                  50 ggg aaa att ctg aaa gac ggg gac acg ctg aac cag cac ggc atc aaa        247
Gly Lys Ile Leu Lys Asp Gly Asp Thr Leu Asn Gln His Gly Ile Lys
     55                  60                  65 gat ggc ctc acc gta cat tta gtc atc aaa aca gca cag aaa tcc cag        295
Asp Gly Leu Thr Val His Leu Val Ile Lys Thr Ala Gln Lys Ser Gln
 70                  75                  80 gac cca tca gcg gtt tcc tct gct tct gtt gcg gct tct tcc gac tcc        343
Asp Pro Ser Ala Val Ser Ser Ala Ser Val Ala Ala Ser Ser Asp Ser
 85                  90                  95                 100 ccc tcg cag aca ggg aac gct acg tcc cag aca ccc tct act ggc aat        391
Pro Ser Gln Thr Gly Asn Ala Thr Ser Gln Thr Pro Ser Thr Gly Asn
                105                 110                 115 ggc tcc tcc gag ggg acc ggt gaa acc aac aga gca acg gct ccc ggc        439
Gly Ser Ser Glu Gly Thr Gly Glu Thr Asn Arg Ala Thr Ala Pro Gly
```

```
Gly Ser Ser Glu Gly Thr Gly Glu Thr Asn Arg Ala Thr Ala Pro Gly
            120                 125                 130 act gct gca aat gga tct ccc gct gcc cca gac ctg ctg tcc gga ttt        487
Thr Ala Ala Asn Gly Ser Pro Ala Ala Pro Asp Leu Leu Ser Gly Phe
            135                 140                 145 ggg ggt ttg tca gga ttg ggc aat ctg ggc atg gga tct tcc aac ttc        535
Gly Gly Leu Ser Gly Leu Gly Asn Leu Gly Met Gly Ser Ser Asn Phe
150                 155                 160 atg gaa ctg cag cag cag atg cag aga cag ctc atg tcc aac ccc gag        583
Met Glu Leu Gln Gln Gln Met Gln Arg Gln Leu Met Ser Asn Pro Glu
165                 170                 175                 180 atg ctg tcc caa att atg gag aac ccc ctg gtg caa aac atg atg tct        631
Met Leu Ser Gln Ile Met Glu Asn Pro Leu Val Gln Asn Met Met Ser
            185                 190                 195 aac ccc gat ctg atg agg cag atg atc ata gcc aat ccg cag atg cag        679
Asn Pro Asp Leu Met Arg Gln Met Ile Ile Ala Asn Pro Gln Met Gln
            200                 205                 210 cag ctc atg gaa agg aac cca gag atc agc cat atg ttg aac aac cca        727
Gln Leu Met Glu Arg Asn Pro Glu Ile Ser His Met Leu Asn Asn Pro
            215                 220                 225 gag ctg atg agg cag act atg gag ttg gct cga aac cct gcc atg atg        775
Glu Leu Met Arg Gln Thr Met Glu Leu Ala Arg Asn Pro Ala Met Met
            230                 235                 240 cag gag atg atg agg aac cag gac cga gcc ctc agc aac cta gaa agc        823
Gln Glu Met Met Arg Asn Gln Asp Arg Ala Leu Ser Asn Leu Glu Ser
245                 250                 255                 260 atc cct ggt gga tac aat gcc ttg cgc cga atg tac aca gac atc cag        871
Ile Pro Gly Gly Tyr Asn Ala Leu Arg Arg Met Tyr Thr Asp Ile Gln
            265                 270                 275 gaa cca atg ttt agt gca gcc aga gaa cag ttt ggc aat aat cct ttt        919
Glu Pro Met Phe Ser Ala Ala Arg Glu Gln Phe Gly Asn Asn Pro Phe
            280                 285                 290 tcc gca tta gcc ggc ggc tca gag ggt tca gcc tca cag cca ctg cgc        967
Ser Ala Leu Ala Gly Gly Ser Glu Gly Ser Ala Ser Gln Pro Leu Arg
            295                 300                 305 aca gag aac agg gag ccg ctc ccc aac ccc tgg agc cca gcc tcg ccc       1015
Thr Glu Asn Arg Glu Pro Leu Pro Asn Pro Trp Ser Pro Ala Ser Pro
            310                 315                 320 tct tcc caa aac cag acg tcc aac agt gaa agc aac act ggc tct acc       1063
Ser Ser Gln Asn Gln Thr Ser Asn Ser Glu Ser Asn Thr Gly Ser Thr
325                 330                 335                 340 acc agc caa agt gtc ccc acc gtg tcc aac cct ctt ggc atc aac gct       1111
Thr Ser Gln Ser Val Pro Thr Val Ser Asn Pro Leu Gly Ile Asn Ala
            345                 350                 355 gcc agt ctg gga aca ggc acc tat aat agc cca gaa atg caa ggc ctg       1159
Ala Ser Leu Gly Thr Gly Thr Tyr Asn Ser Pro Glu Met Gln Gly Leu
            360                 365                 370 ttg cag cag atc acg gaa aac ccc cag tta ata cag agt atg att tct       1207
Leu Gln Gln Ile Thr Glu Asn Pro Gln Leu Ile Gln Ser Met Ile Ser
            375                 380                 385 gcc ccc tac acg cgg agt atg atg cag gcc atg gcg cag aac cca gaa       1255
Ala Pro Tyr Thr Arg Ser Met Met Gln Ala Met Ala Gln Asn Pro Glu
            390                 395                 400 ttt act gca cag atg atg ggg aac att cca atc ttc tct ggg aac ccg       1303
Phe Thr Ala Gln Met Met Gly Asn Ile Pro Ile Phe Ser Gly Asn Pro
405                 410                 415                 420 cag cta cag gaa cag ctt cga cac caa ctg cca gtc ttc ctg cag cag       1351
Gln Leu Gln Glu Gln Leu Arg His Gln Leu Pro Val Phe Leu Gln Gln
            425                 430                 435
```

```
atg cag aac cca gaa tct atg tca gta atg agt aac ccc agg gcg atg     1399
Met Gln Asn Pro Glu Ser Met Ser Val Met Ser Asn Pro Arg Ala Met
        440                 445                 450 cag gcg ctg ctc cag gtc caa cag gga ctt cag aca ctg cag act gag     1447
Gln Ala Leu Leu Gln Val Gln Gln Gly Leu Gln Thr Leu Gln Thr Glu
            455                 460                 465 gcc ccg ggc ttg tta tcc agc ctc ggt tcc gtt gga atc cct ggg gtc     1495
Ala Pro Gly Leu Leu Ser Ser Leu Gly Ser Val Gly Ile Pro Gly Val
        470                 475                 480 cca ccc acg tct ggt gga agt aca gcc cct gaa aac ccc gcc tct tcc     1543
Pro Pro Thr Ser Gly Gly Ser Thr Ala Pro Glu Asn Pro Ala Ser Ser
485                 490                 495                 500 tcc aca cca tca agt gcc tct cca tca ggg ggc agc agc agc aac aat     1591
Ser Thr Pro Ser Ser Ala Ser Pro Ser Gly Gly Ser Ser Ser Asn Asn
            505                 510                 515 ccc cag caa cag atg atg cag cag atg ata caa ctt ttg gcc ggg ggt     1639
Pro Gln Gln Gln Met Met Gln Gln Met Ile Gln Leu Leu Ala Gly Gly
        520                 525                 530 aat tct cag gtg cag aac ccc gag gtc cgt ttc cag tct cag ctg gac     1687
Asn Ser Gln Val Gln Asn Pro Glu Val Arg Phe Gln Ser Gln Leu Asp
            535                 540                 545 cag ctc aac gcc atg ggg ttt atc aac cgg gaa gca aat gta cag gcc     1735
Gln Leu Asn Ala Met Gly Phe Ile Asn Arg Glu Ala Asn Val Gln Ala
        550                 555                 560 ctt ata gct act ggg ggc gac atc aat gct gcc atc gag aga ctg ttg     1783
Leu Ile Ala Thr Gly Gly Asp Ile Asn Ala Ala Ile Glu Arg Leu Leu
565                 570                 575                 580 ggc tcc cag ccc tcc taa tgagacagag agcgagagct tgcccaaaa             1831
Gly Ser Gln Pro Ser
                585 tctacaggaa cacattctcc ctgactcgcc atgccccacc gccgagcatc atgggacgtg   1891 gctgactgct gcttattgga ctgttcctat tggatcccag gtgacatgtg gatgctcagt   1951 gctgtgtggg acactacctg tatcatctcc cccatcccga gggtcgccgc ccctctatta   2011 caggtccccc tcagctttcc ttcctgatgc tgttaataaa caaccccataa accaagccgc   2071 tatatagcaa catttgctcg catctactat taactatta actcactaat tctccgataa    2131 actcagctca aattctggtc tcagttatgt aggttatttt tttcctccct tcttcactgt   2191 tttgccttta acccctcccc gatggcctaa tgcattggag ctgtattttc attagattga   2251 tttttatcaa taaatcaacg aatttttattt ttaacaaaaa aaaaaaaaaa aaaaaaaaa   2311

<210> SEQ ID NO 20
<211> LENGTH: 585
<212> TYPE: PRT
<213> ORGANISM: Xenopus laevis

<400> SEQUENCE: 20

Met Ala Glu Ser Gly Ala Asp Gly Ala Ala Ser Gly Thr Thr Gly Pro
1               5                   10                  15

Ala Pro Gly Lys Gly Leu Ile Arg Val Thr Val Lys Thr Pro Lys Asp
            20                  25                  30

Lys Glu Glu Ile Ser Arg Arg Phe Lys Ala Lys Arg Asp Gln Leu Val
        35                  40                  45

Leu Ile Phe Ala Gly Lys Ile Leu Lys Asp Gly Asp Thr Leu Asn Gln
    50                  55                  60

His Gly Ile Lys Asp Gly Leu Thr Val His Leu Val Ile Lys Thr Ala
65                  70                  75                  80
```

-continued

```
Gln Lys Ser Gln Asp Pro Ser Ala Val Ser Ala Ser Val Ala Ala
                85                  90                  95

Ser Ser Asp Ser Pro Ser Gln Thr Gly Asn Ala Thr Ser Gln Thr Pro
            100                 105                 110

Ser Thr Gly Asn Gly Ser Ser Glu Gly Thr Gly Glu Thr Asn Arg Ala
        115                 120                 125

Thr Ala Pro Gly Thr Ala Ala Asn Gly Ser Pro Ala Ala Pro Asp Leu
    130                 135                 140

Leu Ser Gly Phe Gly Gly Leu Ser Gly Leu Gly Asn Leu Gly Met Gly
145                 150                 155                 160

Ser Ser Asn Phe Met Glu Leu Gln Gln Met Gln Arg Gln Leu Met
            165                 170                 175

Ser Asn Pro Glu Met Leu Ser Gln Ile Met Glu Asn Pro Leu Val Gln
            180                 185                 190

Asn Met Met Ser Asn Pro Asp Leu Met Arg Gln Met Ile Ile Ala Asn
            195                 200                 205

Pro Gln Met Gln Gln Leu Met Glu Arg Asn Pro Glu Ile Ser His Met
    210                 215                 220

Leu Asn Asn Pro Glu Leu Met Arg Gln Thr Met Glu Leu Ala Arg Asn
225                 230                 235                 240

Pro Ala Met Met Gln Glu Met Met Arg Asn Gln Asp Arg Ala Leu Ser
                245                 250                 255

Asn Leu Glu Ser Ile Pro Gly Gly Tyr Asn Ala Leu Arg Arg Met Tyr
            260                 265                 270

Thr Asp Ile Gln Glu Pro Met Phe Ser Ala Ala Arg Glu Gln Phe Gly
    275                 280                 285

Asn Asn Pro Phe Ser Ala Leu Ala Gly Gly Ser Glu Gly Ser Ala Ser
    290                 295                 300

Gln Pro Leu Arg Thr Glu Asn Arg Glu Pro Leu Pro Asn Pro Trp Ser
305                 310                 315                 320

Pro Ala Ser Pro Ser Ser Gln Asn Gln Thr Ser Asn Ser Glu Ser Asn
                325                 330                 335

Thr Gly Ser Thr Thr Ser Gln Ser Val Pro Thr Val Ser Asn Pro Leu
            340                 345                 350

Gly Ile Asn Ala Ala Ser Leu Gly Thr Gly Thr Tyr Asn Ser Pro Glu
            355                 360                 365

Met Gln Gly Leu Leu Gln Gln Ile Thr Glu Asn Pro Gln Leu Ile Gln
    370                 375                 380

Ser Met Ile Ser Ala Pro Tyr Thr Arg Ser Met Met Gln Ala Met Ala
385                 390                 395                 400

Gln Asn Pro Glu Phe Thr Ala Gln Met Met Gly Asn Ile Pro Ile Phe
                405                 410                 415

Ser Gly Asn Pro Gln Leu Gln Glu Gln Leu Arg His Gln Leu Pro Val
            420                 425                 430

Phe Leu Gln Gln Met Gln Asn Pro Glu Ser Met Ser Val Met Ser Asn
    435                 440                 445

Pro Arg Ala Met Gln Ala Leu Leu Gln Val Gln Gln Gly Leu Gln Thr
    450                 455                 460

Leu Gln Thr Glu Ala Pro Gly Leu Leu Ser Ser Leu Gly Ser Val Gly
465                 470                 475                 480

Ile Pro Gly Val Pro Pro Thr Ser Gly Gly Ser Thr Ala Pro Glu Asn
                485                 490                 495

Pro Ala Ser Ser Ser Thr Pro Ser Ser Ala Ser Pro Ser Gly Gly Ser
```

-continued

```
            500                 505                 510
Ser Ser Asn Asn Pro Gln Gln Gln Met Met Gln Gln Met Ile Gln Leu
        515                 520                 525

Leu Ala Gly Gly Asn Ser Gln Val Gln Asn Pro Glu Val Arg Phe Gln
    530                 535                 540

Ser Gln Leu Asp Gln Leu Asn Ala Met Gly Phe Ile Asn Arg Glu Ala
545             550                 555                 560

Asn Val Gln Ala Leu Ile Ala Thr Gly Gly Asp Ile Asn Ala Ala Ile
                565                 570                 575

Glu Arg Leu Leu Gly Ser Gln Pro Ser
            580                 585
```